(12) United States Patent
Habarakada Layanage et al.

(10) Patent No.: US 11,846,599 B2
(45) Date of Patent: Dec. 19, 2023

(54) CARTRIDGE AND SYSTEM FOR DETECTING AN ANALYTE IN A BODILY FLUID SAMPLE AT POINT-OF-CARE BIOSENSING

(71) Applicant: Early Is Good Inc., Indianapolis, IN (US)

(72) Inventors: Thakshila Udayakanthi Habarakada Layanage, Indianapolis, IN (US); Asel Ananda Habarakada Layanage, Indianapolis, IN (US); Nisal Ananda Habarakada Layanage, Seoul (KR)

(73) Assignee: Early is Good Inc., Indianapolis, IN (US)

( * ) Notice: Subject to any disclaimer, the term of this patent is extended or adjusted under 35 U.S.C. 154(b) by 248 days.

(21) Appl. No.: 17/093,033

(22) Filed: Nov. 9, 2020

(65) Prior Publication Data
US 2021/0140911 A1   May 13, 2021

Related U.S. Application Data

(60) Provisional application No. 62/931,944, filed on Nov. 7, 2019.

(51) Int. Cl.
*G01N 27/327* (2006.01)
*G01N 33/52* (2006.01)
*G01N 33/543* (2006.01)

(52) U.S. Cl.
CPC ..... *G01N 27/3272* (2013.01); *G01N 27/3274* (2013.01); *G01N 33/52* (2013.01); *G01N 33/5438* (2013.01); *G01N 33/54388* (2021.08)

(58) Field of Classification Search
None
See application file for complete search history.

(56) References Cited

PUBLICATIONS

J. Sun, et al., "Using fluorescence immunochromatographic test strips based on quantum dots for the rapid and sensitive determination of microcystin-LR", Analytical and Bioanalytical Chemistry, 409(8): p. 2213-2220, Mar. 2017.*
Pisanic II, T.R. et al., Quantam Dots in Diagnostics and Detection: Principles and Paradigms, Analyst. Jun. 21, 2014; 139(12): 2968-2981. doi: 10.1039/c4an00294f., pp. 1-33.
Sajid, Muhammad et al., Designs, Formats and Applications of Lateral Flow Assay: A Literature Review, King Saud University, Journal of Saudi Chemical Society (2015) 19, pp. 689-705.
Smith, Andrew M. et al., Semiconductor Nanocrystals: Structure, Properties, and Band Gap Engineering, Accounts of Chemical Research, Feb. 2010, vol. 43, No. 2, pp. 190-200.
England, Christopher G. et al., NanoLuc: A Small Luciferase is Brightening up the Field of Bioluminescence, Bioconjug Chem., Author Manuscript, May 18, 2017, pp. 1-29.
Koczula, Katarzyna M. et al., Lateral Flow Assays, Essays in Biochemistry, Portland Press Limited on behalf of the Biochemical Society, 2016, 60, DOI: 10.1042/EBC20150012, pp. 111-120.
Liu, Yanting et al., Microfluidics-Based Plasomic Biosensing System Based on Patterned Plasmonic Nanostructure Arrays, Micromachines 2021, 12, 826, MDPI, pp. 1-20.

* cited by examiner

*Primary Examiner* — J. Christopher Ball
(74) *Attorney, Agent, or Firm* — Ice Miller LLP

(57) ABSTRACT

The present invention relates to a biosensor and system for detecting an analyte in a bodily fluid sample for at-home point-of-care diagnosis.

36 Claims, 21 Drawing Sheets
(14 of 21 Drawing Sheet(s) Filed in Color)
Specification includes a Sequence Listing.

SEQ ID NO: 20
SEQ ID NO: 15
SEQ ID NO: 19
SEQ ID NO: 16
SEQ ID NO: 17
SEQ ID NO: 18

CARTRIDGE AND SYSTEM FOR DETECTING AN ANALYTE IN A BODILY FLUID SAMPLE AT POINT-OF-CARE BIOSENSING

CROSS-REFERENCE TO RELATED APPLICATIONS

This application claims priority under 35 U.S.C. § 119(e) to provisional U.S. Application No. 62/931,944, filed Nov. 7, 2019, the entire disclosure of which is incorporated herein by reference.

SEQUENCE LISTING

The instant application contains a Sequence Listing which has been submitted electronically in ASCII format and is hereby incorporated by reference in its entirety.

BACKGROUND

Technical Field: The field of the disclosure is biosensing. More particularly, the disclosure relates to lateral flow assay based at home point of care diagnosis.

In today's rapidly increasing demand for remote high-tech medical devices due to greater interest in health and growing aging population, biosensor technology is advancing towards detecting or sensing personalized disease and health related biomarker components (e.g., presence or absence of cancer marker protein and concentration analysis, optimal biological ion concentration, blood sugar level, etc.) from urine, saliva, or blood.

Furthermore, attempts are being made with an aim to implement such biosensor technology into a personalized diagnosis device and shift the existing healthcare institution-focused system into the next generation biosensor monitoring system focusing on patient service.

Specifically, the discovery of multiple disease biomarkers and the establishment of micro fluid system has paved the way for the development of a method and system for predicting, diagnosing, and treating disease at a point-of-care (POC) environment. POC system is particularly suitable for today's medical environment as it can deliver testing results to medical practitioners and patients quickly. If early diagnosis is enabled by such POC system, early treatment by medical practitioners can prevent the condition of a patient from worsening due to the neglect of the disease. In addition, POC system enables early diagnosis of a disease or the progress of a disease, allowing medical practitioners to initiate or modify treatment in a timely manner. Notwithstanding the advantages described above, however the weakness of a POC system includes the high cost of manufacturing the system (particular, the components of the device) and the low detection sensitivity of the system. Here in this work we have proposed using 5 different types of biomarkers in a one assay for the early and accurate diagnosis of bladder cancer. Accordingly, five different types of biomarkers are: On microRNAs, long noncoding RNA, Circulating DNA and proteins.

microRNAs are small noncoding RNAs which has the capability of regulating messenger RNA and translational process hence release to the blood circulation and remarkable stable in bodily fluids. Also, microRNAs are key regulators in numerous biological processes including gene expression. Altogether changes of microRNAs levels in biological samples including urine, saliva, plasma can serve an early diagnostic tool for the accurate diagnosis and it has been identified as a wide range of diseases including cancer, diabetes, heart disease, Alzheimer's disease and etc. Beside that stability of microRNA in biological samples have been identified as remarkably stable. Quantitative measurement of miRs in unmodified biological samples (urine, plasma, saliva etc.) crucial for developing a at home point of care diagnostic tool. Gold standard of microRNA detection techniques such as microarrays and qRT-PCR techniques are not applicable to at home point of care diagnosis applications as they involved with sophisticated instrumentation and sample preparation steps. most of the other techniques such as fluorescence-, electronic-, electrochemical-, silicon nanowire-, microring resonator-, microcantilever-, and nanopore-based techniques for analyzing microRNAs have been reported in point of care applications, however achieving the sensitivity, accuracy of diagnosis remain challenging. Over expressed miRNAs in cancers, may function as oncogenes and promote cancer development by negatively regulating tumor suppressor genes and/or genes that control cell differentiation or apoptosis. Under expressed miRNAs in cancers, function as tumor suppressor genes and may inhibit cancers by regulating oncogenes and/or genes that control cell differentiation or apoptosis. Therefore, miRNA expression profiles may become useful biomarkers for cancer diagnostics. In addition, miRNA therapy could be a powerful tool for cancer prevention and therapeutics.

Long non-coding RNAs (lncRNA) are also a type of RNA, which has a length more than 200 nucleotides that are not translated into protein. lncRNAs are involved in many biological processes including transcriptional and posttranscriptional regulators which further control the gene expression in a spatial, temporal, and cell context-dependent manner. Therefore, the deviation of the expression levels of lncRNAs is further link with several diseases including cardiac dysfunction, diabetes, liver fibrosis and cancer. In cancer, lncRNA controls many molecular processes which regulates the cell proliferation, invasion, metastasis and apoptosis. Therefore, lncRNAs stands as an ideal diagnostic marker for early diagnosis as they are readily available in biological samples which have mentioned in section Furthermore, unlike microRNA, lncRNA itself is a functional molecule therefore its expression level may be a better indicator of the diseases. There are two common methods available for the lncRNAs detection such as microarrays and RNA sequencing (RNA-seq) using next generation sequencers. However, these methods are semiquantitative, require sequence-based amplification and radioactive labeling steps, and suffer from cross-hybridization and invalid internal controls. Further they are suffering from low sensitivity and challenging utilized in physiological media. Altogether, there is an unmet requirement to develop highly sensitive assay for long noncoding detection at real biological sample and especially to the best of our knowledge it has not reported of utilizing lncRNA in a at home point of care diagnostic tools.

Proteins can be identified as the key compound in biosynthesis, organ signal, cell, and tissue. Additionally, it provides structural stability to the cell and tissues in living organisms. However, due to the complexity of the structure and the function of protein, proteome study remains challenging. These proteins are abundantly present in the biological samples as mentioned in section [0001] Even though proteins are secreted in cellular organs as explained earlier, some of them are specially secreted under pathological conditions including cancer, diabetes and Alzheimer's disease, This is mainly due to the alternative microRNA synthesis and other chromosomal genetic variations. Therefore, disease specific proteins can be identified as a biomarker for cancer diagnosis and will be a presence in all biological specimen presence. as massspectrometry (MS), selected reaction monitoring (SRM) or multiple reaction microarrays (MRM), western blotting techniques enzyme-linked immunosorbent assay (ELISA) can be identified as the techniques for protein monitoring. Among these techniques LC/MS and some other techniques brings certain barriers such as the requirement of the skill set and specialty of the scientist and the cost and availability of instruments. Also, the other techniques associated with drawbacks such as in adequacies in sensitivity to assay low abundance of biomarkers with high specificity and accuracy and less reproducibility as well as factors related to the biobanking of samples, including limited sample volume, the range of sample types, are also challenging.

Bladder cancer (BC) is the fourth most common cancer in men. The American Cancer Society's estimates About 81,400 new cases of bladder cancer (about 62,100 in men and 19,300 in women) and About 17,980 deaths from bladder cancer (about 13,050 in men and 4,930 in women) in the United States for 2020.cystoscopy is gold standard method of evaluating the bladder and the urethra and diagnosing and monitoring bladder cancer. The cystoscope, a long thin camera, is inserted through the urethra into the bladder. During the cystoscopy, the urologist will look through the cystoscope and make a note of anything in the bladder that may be abnormal. If a tumor or other abnormality is identified, the urologist will likely schedule you for a cystoscopy under anesthesia with bladder biopsy or "transurethral resection of bladder tumor (TURBT)." Which then continue for biopsy for the further confirmation. This procedure only allows to symptom base diagnosis and it is invasive where patient discomfort will remain for 3-5 days with bleeding and irritating. Other than the cystoscopy CT urogram which is radiological test to explore possible reasons for blood in the urine or other symptoms or MRI scan of the tumor imaging are common techniques that used for the bladder cancer diagnosis. However, these techniques involve with severe patient discomfort and side effect of radiation etc. Majorly the diagnosis is based on the symptoms and early and accurate diagnosis is not possible with such techniques.

BC is identified as the highly recurring cancer and it is required intensive follow-up program, through cystoscopy and urinary cytology and as a results BC remains as the most expensive follow-up, in comparison to other cancers. urine cytology is noninvasive method for the diagnosis but has very poor sensitivity (less than 40%) towards diagnosis. Regardless of the sensitivity limitations, urine cytology is still considered as the standard of care to detect BC. However, use of new methodologies in the follow-up of patients through low cost, non-invasive, easy to use procedure with high sensitivity and high selectivity remains as unmet challenge for the BC which will help surpass the current limitations of BC follow-up. This type of technology will be highly beneficials for early and accurate at home diagnosis of BC and follow-up of BC patients for advanced diagnosis and diagnosis of recurrence of the disease in a cost-effective way.

Biomarker based diagnosis is a promising method for early and accurate diagnosis of BC. Several studies are being developed to enlarge the diagnostic accuracy of urinary tests and the creation of alternatives to cytology and/or cystoscopy. A vast quantity of potential biomarkers is described in the literature aiming to detect genomic, transcriptomic, epigenetic or protein changes in serum or in urine sample.

Polymerase chain reaction (qRT-PCR) assay and Microarray commonly used for microRNA diagnosis but limited with semiquantitative method and essential to have sequence-based amplification and purification or radioactive labeling step. Possible draw backs are cross-hybridization and high expense and challenge to adopt in miniaturized systems. Additionally, electrochemical, and fluorescence-based assays are also available for microRNA detection but still limited with draw backs including challenges of using in direct human samples.

In today's rapidly increasing demand for remote high-tech medical devices due to greater interest in health and growing aging population, biosensor technology is advancing towards detecting or sensing personalized disease and health related biomarker components (e.g., presence or absence of cancer marker protein and concentration analysis, optimal biological ion concentration, blood sugar level, etc.) from urine, saliva, or blood.

Furthermore, attempts are being made with an aim to implement such biosensor technology into a personalized diagnosis device and shift the existing healthcare institution-focused system into the next generation biosensor monitoring system focusing on patient service. Among most of the POC development strategies lateral flow assay based POC devices are the rapidly growing strategies. Further, microfluidics, nanorobotics is the rising field in this concept. These strategies helped to overcome the drawbacks associated with currently available conventional clinical techniques such as enzyme linked immunosorbent assay (ELISA). Those advantageous can be identified as the rapidity and one step analysis, low operational cost, simple instrumentation, user friendly format, less or no interference due to chromatographic separation. However, when a POC device adapt to the at home diagnostic tool, it should provide convenient, noninvasive, confirms to current clinical practice, enables real time disease monitoring and the study of tumor evolution, and should have high specificity, ultrasensitivity, high accuracy, high precision long shelf life with stability under different set of environmental conditions. Accordingly, it would be beneficial to design at home point of care diagnostic tool which has the capability of detecting cancer at a very early stage by addressing above mentioned drawbacks

BRIEF DESCRIPTION OF THE DRAWINGS

The patent or application file contains at least one drawing executed in color. Copies of this patent or patent application publication with color drawing(s) will be provided by the Office upon request and payment of the necessary fee.

The above and other objects, features and advantages of the present invention will become more apparent to those of ordinary skill in the art by describing exemplary embodiments thereof in detail with reference to the accompanying drawings, in which:

FIG. 14 and FIG. 15 are schematic views of analytes being bound to $1^{st}$ GQDs illustrated FIG. 2 during the optimization and these GQDs include in the second region/conjugate pad

FIG. 19 and FIG. 20 are ready to bind with GQDs shown in FIG. 17 and FIG. 18. As an example, here the schematic representation is shown with the Au TNPs, same experiment repeated with Au SPs.

FIGS. 21 and 22 are bound with GQDs shown in FIG. 17 and FIG. 18. As an example, here the schematic representation is shown with the Au TNPs, same experiment repeated with Au SPs. Luciferase is in active phase.

SUMMARY OF THE PRESENT INVENTION

Figure 1:
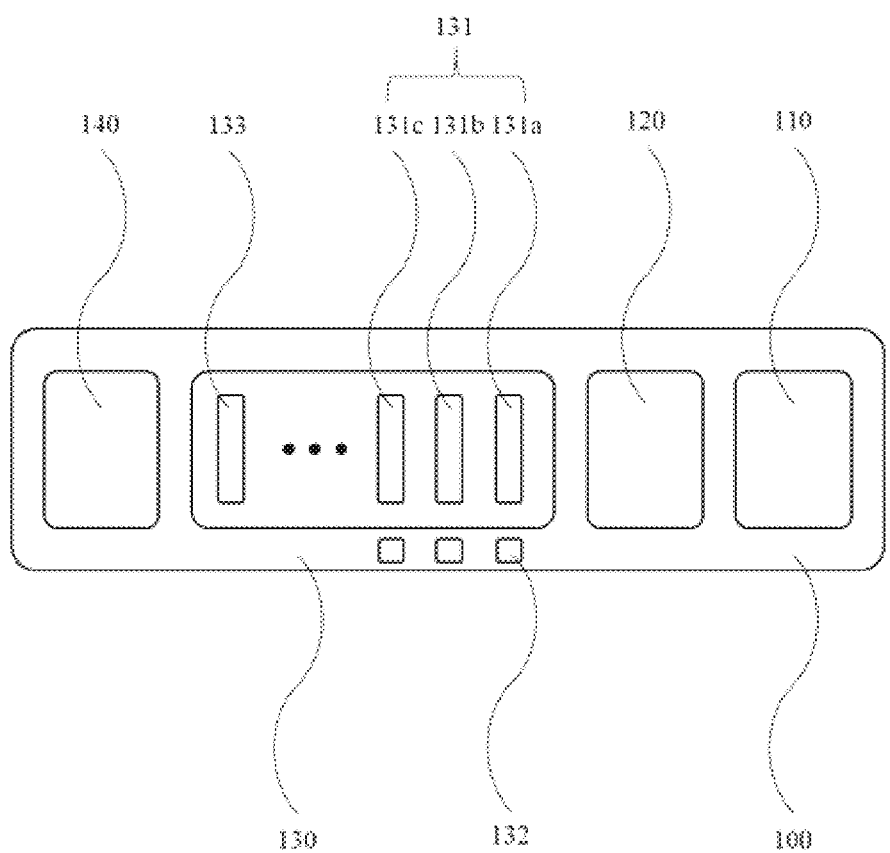
FIG. 1 shows the schematic view of the cartridge.

The present disclosure overcomes the aforementioned drawbacks by providing systems and methods for lateral flow assay technology for accurate diagnosis of biomarkers associated with bladder cancer. In another aspect, this disclosure provides a method of detecting the presence and quantifying amount of microRNA (oncogenic and tumor suppressor), long noncoding RNAs and proteins in urine.

Numerous benefits brought by POC system allow continuous research to be conducted in the related fields and the present invention also provides alternative designs of POC system. According to the present invention, a cartridge and system for detecting an analyte in a bodily fluid sample is provided.

More specifically, according to one aspect of the present invention, a cartridge for detecting an analyte in a bodily fluid sample is provided, comprising i) a first region housing the bodily fluid sample; ii) a second region positioned downstream of said first region, wherein said bodily fluid sample housed in the first region is moved by the lateral flow capillary action, and graphene quantum dot(GQD) mixture containing at least one GQD specific to at least one analyte of said bodily fluid sample in said second region; iii) a third region positioned downstream of said second region, wherein said GQD to which said analyte is bound and/or said GQD to which said analyte is not bound in said second region are moved by the lateral fluid capillary action, and at least one reaction strip that detects the presence of said GQD to which said analyte is bound and a control strip that detects the presence of said GQD to which said analyte is not bound in said third region.

According to another aspect of the present invention, a POC system is provided, comprising i) a cartridge as described above; ii) at least one cartridge chamber into which said cartridge is inserted; and iii) a detection assembly that individually detects a light signal emitted by at least one reaction strip in said cartridge inserted into said cartridge chamber. In yet another aspect, this disclosure provides a method of diagnosing a disease state in a subject, wherein the disease state is indicated by the presence or level of a five different types biomarkers of interest in a urine sample from the subject. The method can include one or more of the following steps: contacting a biosensor with the urine sample, the biosensor including a plurality of graphene quantum dots in the conjugate region, each graphene quantum dots having a functional surface functionalized by either plurality of single-stranded DNA (ssDNA) that is complementary to at least a portion of the microRNA or long non coding RNA or interest antibodies that is specific to the protein of interests. Additionally, each GQDs functionalized with luciferase which ultimately measuring a relative light intensity unit (RLU) of each test strips, the RLU based calibration curve use to determining a concentration of the microRNA, Long Non coding RNAs and proteins presence in the urine sample.

In another aspect, this disclosure provides a cartridge kits that contains biosensor and a plurality of GQDs functionalized with single stranded DNA/PEG spacer/luciferase tag or GQDs functionalized with antibody/PEG spacer/luciferase tag.

The foregoing and other aspects and advantageous of the disclosure will appear from the following experimental method and the description. In the description, reference is made to the accompanying drawings which form a part hereof, and which is shown by way of illustration a preferred aspect of the disclosure. Such aspect does not necessarily represent the full scope of the disclosure.

A representative listing of sequence identifiers is as follows:

NO: 1 is modified ssDNA-10b with a 3' $NH_2$ Modification
NO: 2 is microRNA-10b
NO: 3: ssDNA10b capturing sequence
NO: 4 is modified ssDNA-145 with a 3' $NH_2$ Modification
NO: 5 is microRNA-145
NO: 6 modified ssDNA linc-UCA1 with 3' $NH_2$ Modification
NO: 7 is long noncoding RNA line UCA
NO: 8 is modified ssDNA X
NO: 9 is antibody NMP 22
NO: 10 is protein NMP22
NO: 11 is antibody BTA
NO: 12 is Protein BTA
NO: 13 is Biotin
NO: 14 is antibody IgG
NO: 15 is Protein IgG

EXPERIMENTAL PROCEDURE AND THE DETAILED DESCRIPTION OF EXEMPLARY EMBODIMENTS

Preparation of the Conjugation Pad

Figure 6:
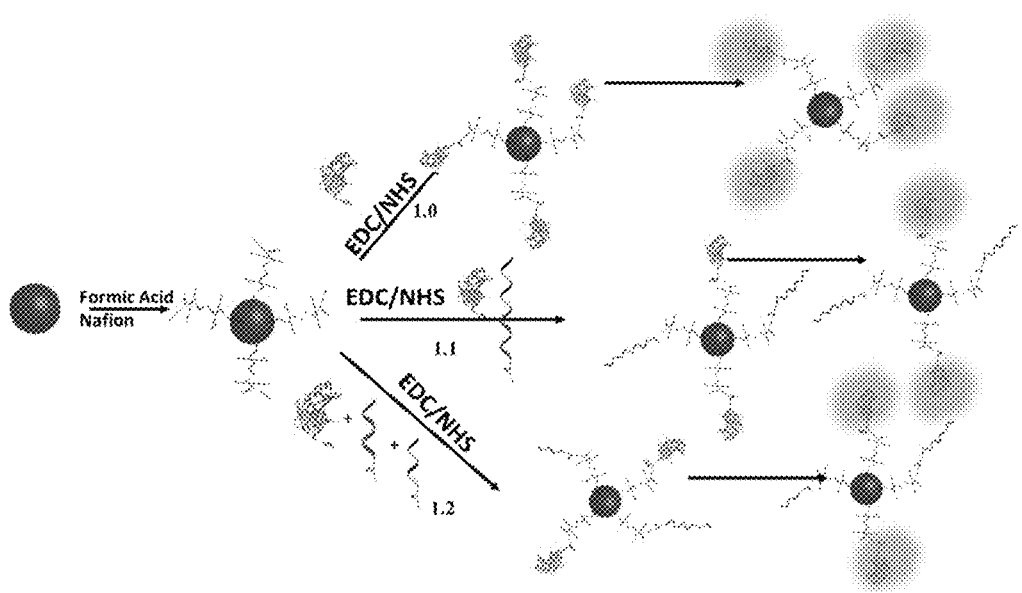
FIG. 6 shows the functionalization scheme of graphene quantum dots with $PEG_8SH$ acid for the preparation of microRNA and long noncoding RNA platform and subsequent functionalization plan for the optimization.
Figure 7:
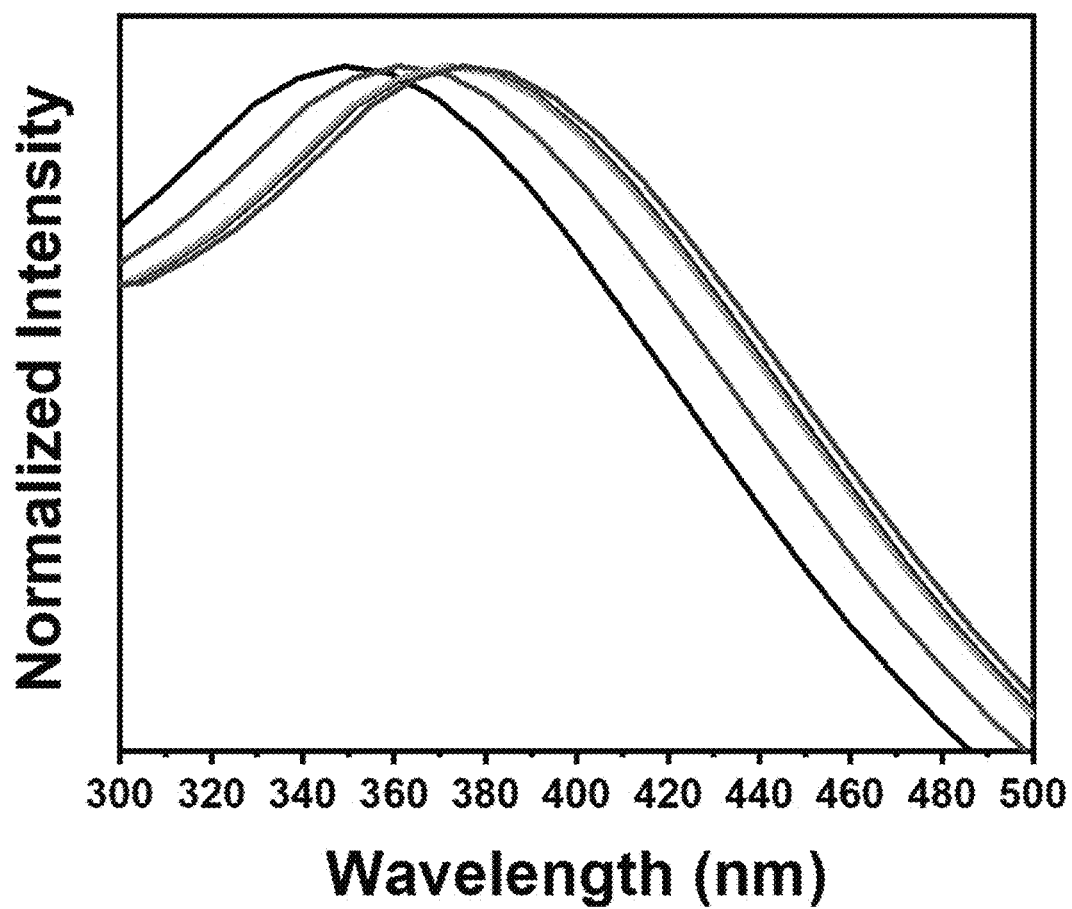
FIG. 7 shows the Absorbance peak changes upon binding with different functionalization steps. Accordingly, GQDs shows absorbance peak appeared at 350 nm and after functionalizing with $PEG_8$ acid it has red shifted 12 nm. Upon functionalizing with luciferase or luciferase and modified ssDNA 10b or Luciferase (1:1), modified ssDNA 10b and ssDNA X (1:1:1) has given 10 nm, 11 nm and 14 nm red shifting from the $PEG_8$ acid peak position respectively.

First part of the work was to do the optimization of conjugate pad preparation. Accordingly, we prepare GQDs conjugation for target analytes for protein, microRNA, and long noncoding RNA. Accordingly, As shown in the FIG. 2, We tried the optimization via three main steps including first started with the functionalization with formic acid and then followed functionalization with 100% luciferase, 1:1 luciferase+NO 9 or luciferase+NO 9+NO 13 (1:1:1). Each functionalized method was observed using LSPR peak shift as shown on the FIG. 3 and obtained shift is summarized on the Table 1. Then we repeated the same experiment where we started from polyethylene glycol functionalized GQDs as a starting material to FIG. out the best functionalizing method to avoid the nonspecific binding and get the highest luciferase intensity for the sensing application FIG. 4. Similarly, each functionalization was observed using LSPR peak shift and showed in FIG. 5. Further obtained LSPR shift were summarized in the Table 2. The obtained shift was better in the case of using PEG-SH and Luciferase intensity was higher when the experiment repeated with PEG-SH. Therefore, for microRNA/lnRNA assay we started with PEG-SH functionalized GQDs and further functionalized with either 100% luciferase, 1:1 luciferase+ssDNA (NO 1) or luciferase+ssDNA 1 (NO 1)+ssDNA 2 (NO 8) (1:1:1) FIG. 6. FIG. 7 and Table 3 explains the LSPR shift and the summary of the shift obtained.

TABLE 1

| Type of functional group | Absorption peak position (nm) | Peak shift (nm) |
|---|---|---|
| GQDs | 350 | |
| GQDs + Acetic Acid | 353 | 3 nm |
| GQDs + Acetic acid + Luciferase | 358 | 8 nm |
| GQDs + Acetic acid + Luciferase + NO 9 | 362 | 12 nm |
| GQDs + Acetic acid + Luciferase + NO 9 + NO 13 | 364 | 14 nm |

TABLE 2

| Type of functional group | Absorption peak position (nm) | Peak shift (nm) |
|---|---|---|
| GQDs | 350 | |
| GQDs + PEG$_8$Acid | 362 | 12 nm |
| GQDs + PEG$_8$Acid + Luciferase | 372 | 10 nm |
| GQDs + PEG$_8$Acid + Luciferase + NO 9 | 387 | 15 nm |
| GQDs + PEG$_8$Acid + Luciferase + NO 9 + NO 13 | 388 | 16 nm |

TABLE 3

| Type of functional group | Absorption peak position (nm) | Peak shift (nm) |
|---|---|---|
| GQDs | 350 | |
| GQDs + PEG8Acid | 362 | 12 nm |
| GQDs + PEG8Acid + Luciferase | 372 | 10 nm |
| GQDs + PEG8Acid + Luciferase + NO 1 | 373 | 11 nm |
| GQDs + PEG8Acid + Luciferase + No 1 + No 8 | 376 | 14 nm |

Figure 9:
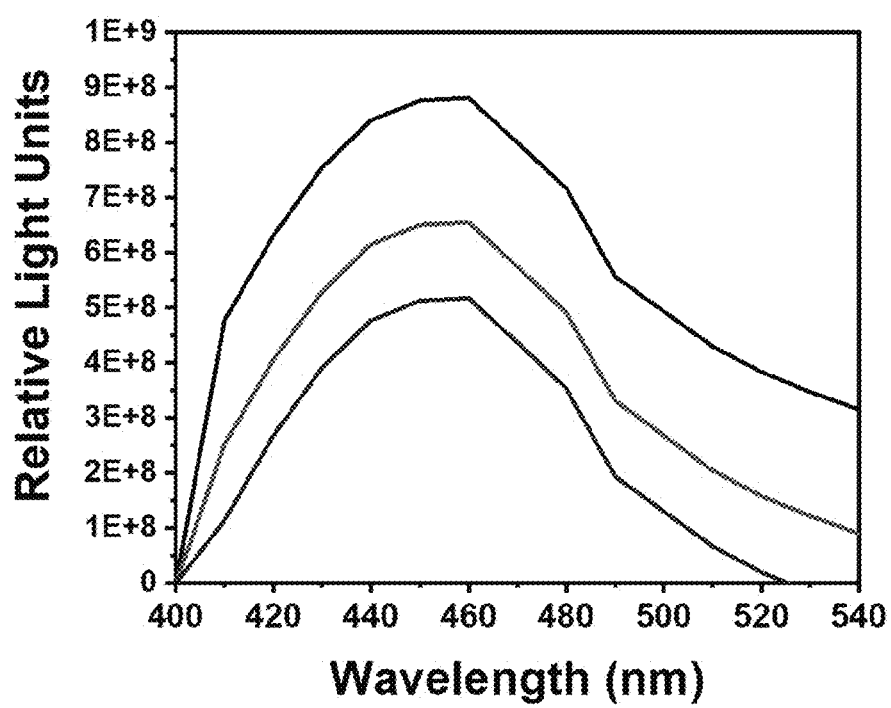
FIG. 9 is recorded light intensity for bioluminescence for $PEG_8$ acetic acid functionalized nanoparticles after binding with 100% Luciferase (black line), Luciferase and modified ssDNA 10b (1:1)-black line and Luciferase, modified ssDNA 10b and ssDNA-X (1:1:1)-blue line.
Figure 10:
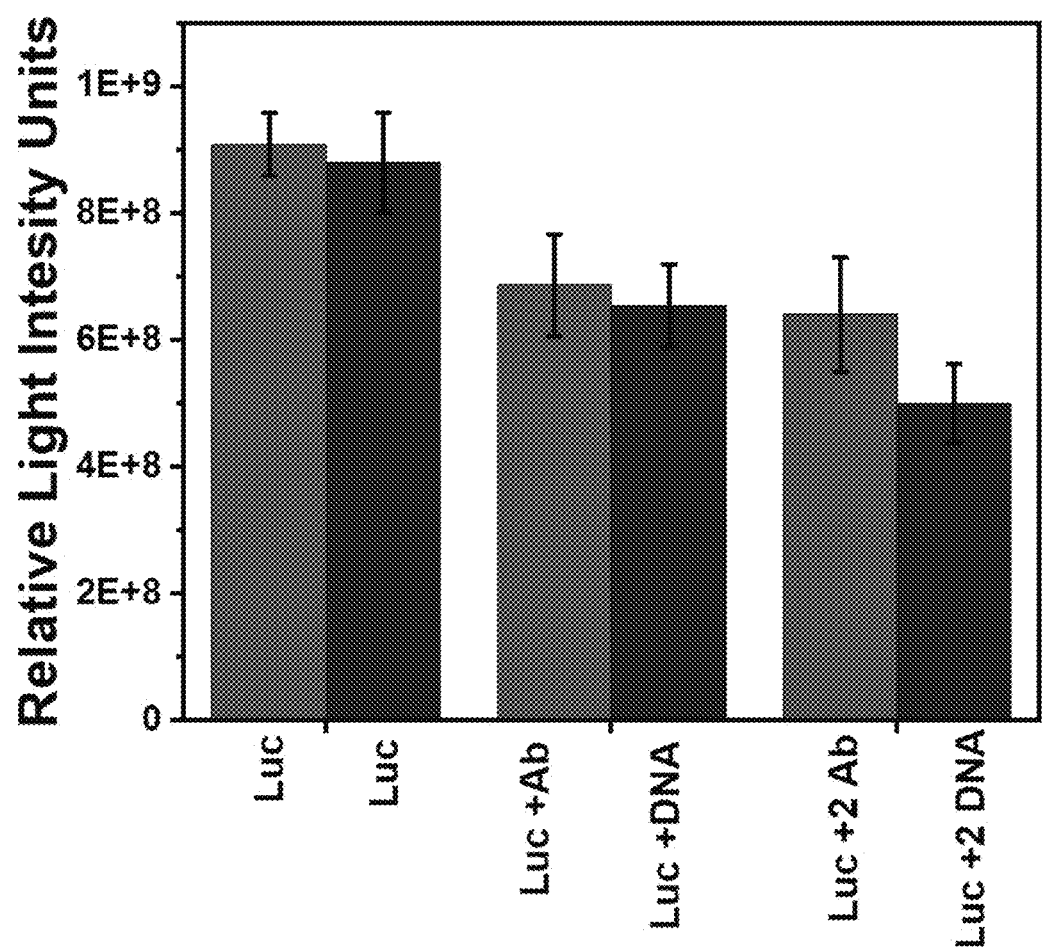
FIG. 10 shows the comparison of Relative Light Intensity Units (RLU) obtained from FIGS. 8 and 9.

By considering all the data then measured luciferase intensity after mixing with the luciferase buffer and luciferin, where it generated bright green color as explained in the below section. The obtained luminescence intensities are summarized in the FIGS. 8, 9 and 10. By considering the obtained (Relative Light Intensity Units) RLU for the bioluminescence reaction we summarized that GQDs functionalized with PEG-SH followed with either 1:1 luciferase and antibody or 1:1 luciferase and ssDNA was given the highest RLU values for the sensor development. All the experimental procedures are summarized in the following section.

Functionalization for Antibodies for GQDs Detection. GQDs were purchased from sigma Aldrich with approximately <5 nm diameter with topographic height of 1-2.0 nm. The obtained GQDs showed average 350 nm absorbance peak. The obtained GQDs had 1 mg/mL concentration and 5 mL of GQDs solution mixed with 40 w/v % of acetic acid and 1% of nafion and ultrasonicated for overnight at 90° C. for overnight. Then obtained mixture was subjected ultracentrifugation for 1 hour at 14000 rpm to separate the functionalized GQDs. The obtained solid redissolved in 10 mM MES buffer at pH 5. Then the solution was mixed with a mixture of 10 mg/mL EDC and 100 mg/mL sulfo-NHS at room temperature for 30 minutes. After that ultra-sonicated for one hour at 14000 rpm and removed the unreacted EDC/NHS-sulfo mixture. Finally, EDC/NHS activated nanoparticles were incubated in 40 mg/mL D-Luciferase or 40 µg/mL luciferase+40 µg/mL anti NMP22 (NO 9) (1:1) ratio or 40 µg/mL luciferase+40 µg/mL anti NMP22+40 µg/mL and biotin antibodies in MES buffer at 37° C. on an orbital shaker for 60 minutes. Finally, the obtained conjugate was centrifuged at 14 000 rpm at 4° C. for 20 min and then washed with 500 µL of bicarbonate buffer (10 mM, pH 8) at 37° C. and 650 rpm for 30 min. The conjugates were then centrifuged (14 000 rpm) at 4° C. for 20 min and blocked with 2% BSA in MES buffer (10 mM, pH 6).

Preparation of PEG$_8$SH Functionalized GQDs for Antibody Detection.

GQDs were purchased from sigma Aldrich with approximately <5 nm diameter with topographic height of 1-2.0 nm. The obtained GQDs showed average 350 nm absorbance peak. The obtained GQDs had 1 mg/mL concentration and 5 mL of GQDs solution mixed with 1 mM PEG$_8$SH for 3 hours and then obtained mixture was subjected ultracentrifugation for 1 hour at 14000 rpm to separate the functionalized GQDs. The obtained solid redissolved in 10 mM MES buffer at pH 5. Then the solution was mixed with a mixture of 10 mg/mL EDC and 100 µg/mL sulfo-NHS at room temperature for 30 minutes. After that ultra-sonicated for one hour at 14000 rpm and removed the unreacted EDC/NHS-sulfo mixture. Finally, EDC/NHS activated nanoparticles were incubated in 40 mg/mL D-Luciferase or 40 µg/mL luciferase+40 µg/mL anti NMP22 (NO 9) (1:1) ratio and 40 mg/mL luciferase+40 µg/mL anti NMP22 (NO 9)+40 µg/mL biotin antibodies (No 13) in MES buffer at 37° C. on an orbital shaker for 60 minutes. Finally, the obtained conjugate was centrifuged at 14 000 rpm at 4° C. for 20 min and then washed with 500 µL of bicarbonate buffer (10 mM, pH 8) at 37° C. and 650 rpm for 30 min. The conjugates were then centrifuged (14 000 rpm) at 4° C. for 20 min and blocked with 2% BSA in MES buffer (10 mM, pH 6).

Functionalization for Gold Nanoparticles for Test Strip

After optimization of the conjugation pad conjugates, next focused was to optimize the test lines in the test strips. Here we proposed to used nanoparticles functionalized antibody/ssDNA to capture either microRNA/long noncoding RNA/proteins. The schematic representation of proposed functionalization is summarized in FIG. 11. Accordingly, we used gold nanoparticles and gold triangular nanoprisms functionalized with PEG-SH for the functionalization steps and further functionalized with either antibody or ssDNA to capture the target conjugates. For the optimization study we focused on used NMP-22 (NO 9) and microRNA 10b (NO 1) as an analyte.

Figure 11:
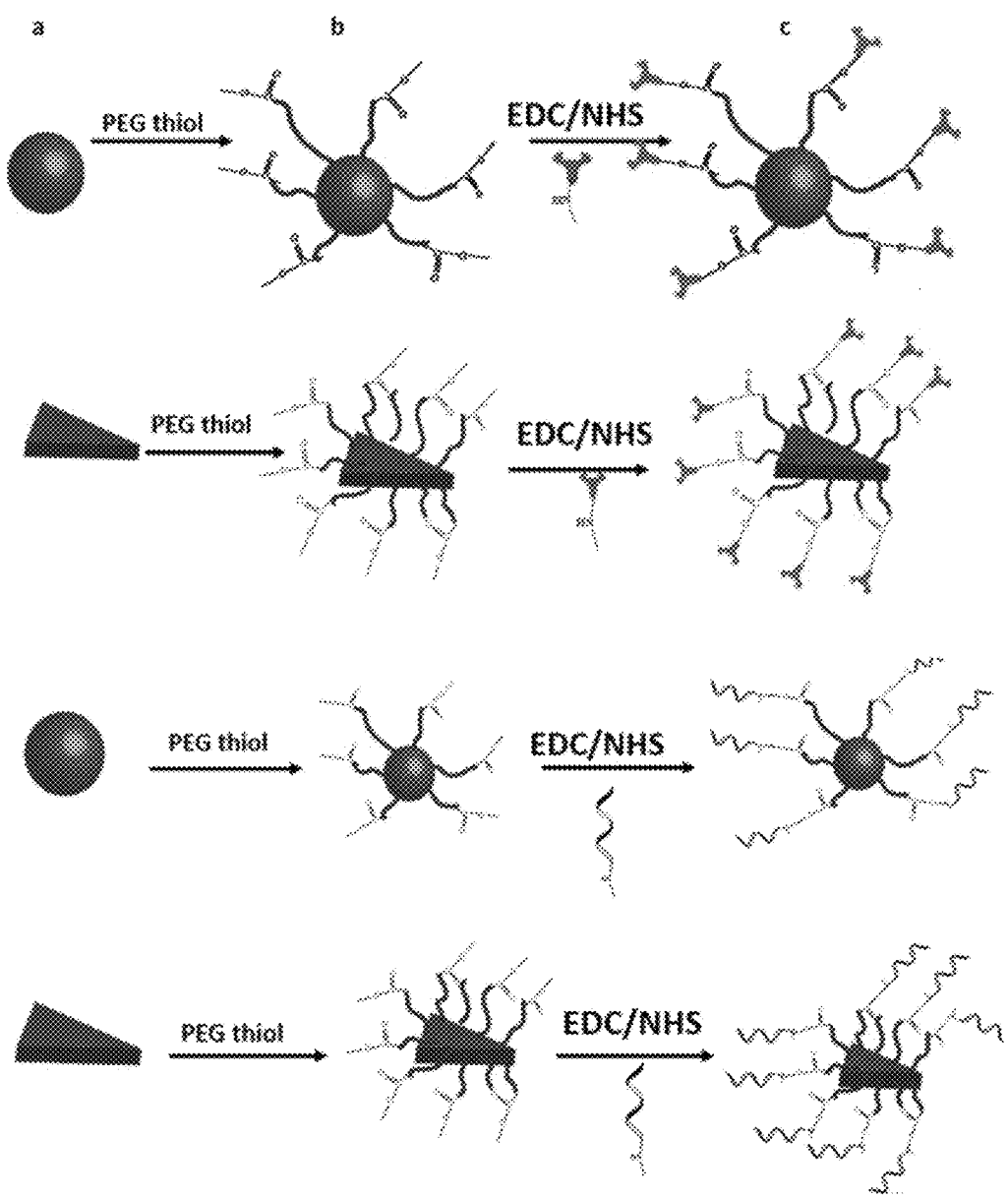
FIG. 11 is a schematic representation of the functionalization steps for the gold nanostructures (Gold spherical particle and Gold triangular nanoprisms) for the test strip preparation to capture the antibodies or ssDNA functionalized nanoparticles Accordingly 1 a-c and 3 a-c shows functionalization steps for the spherical particles for capturing antibody functionalized GQDs and ssDNA functionalized GQDs respectively. Similarly, 2 a-c and 4 a-c shows the functionalization steps for the gold triangular nanoprisms for capturing antibody functionalized GQDs and ssDNA functionalized GQDs, respectively.
Figure 12:
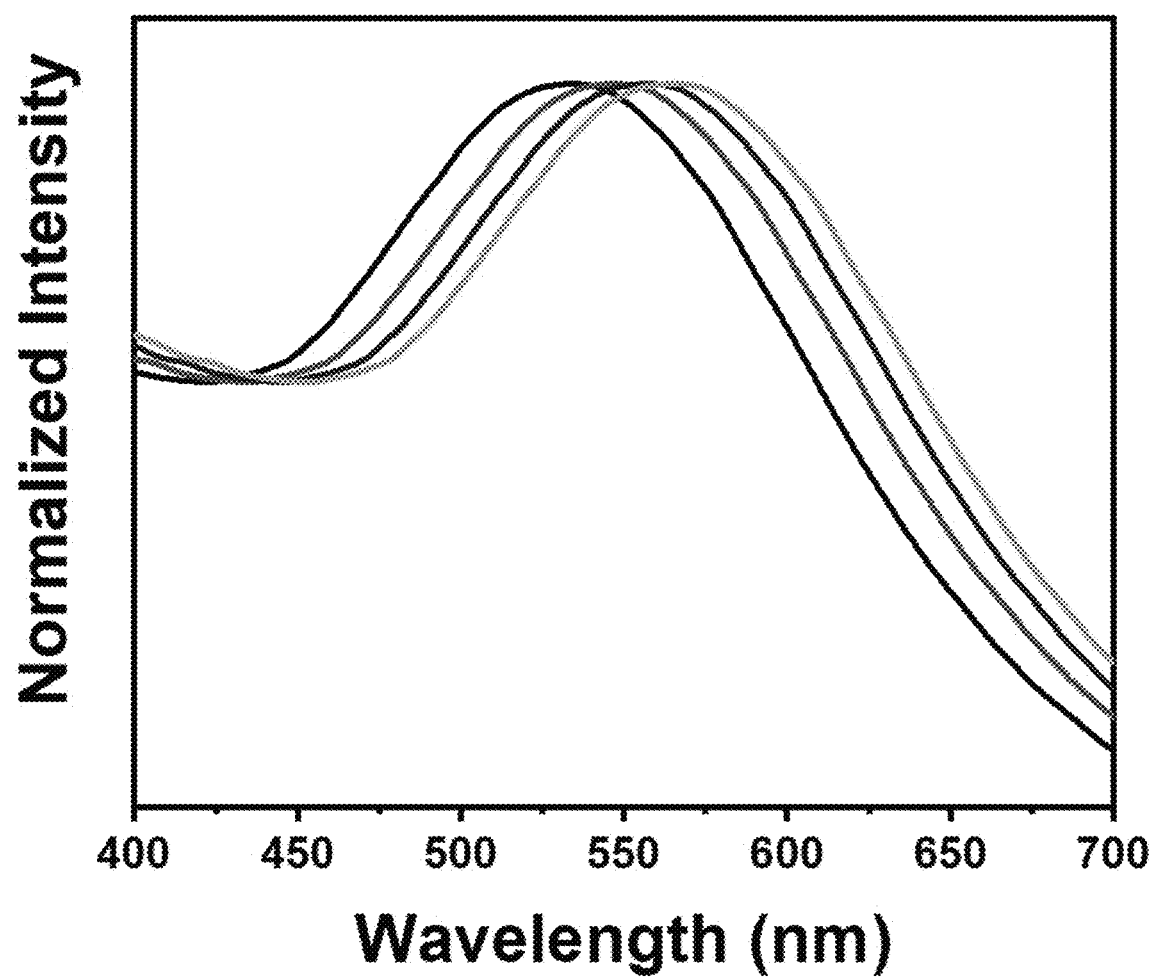
FIG. 12 shows the spectral changes of Au SPs functionalization for test strip to capture the antibody/modified ssDNA. Accordingly, the LSPR peak position was obtained at 530 nm black line and upon PEGylated in solution phase average 13 nm red shift was observed (red line) Then functionalized with antibody NMP22 average 10 nm further redshift was observed (red line) and when it functionalized with modified ssDNA 10b only 8 nm LSPR peak red shift was observed (green line) (later shifts compare to LSPR peak of after PEGylating Au SPs).
Figure 13:
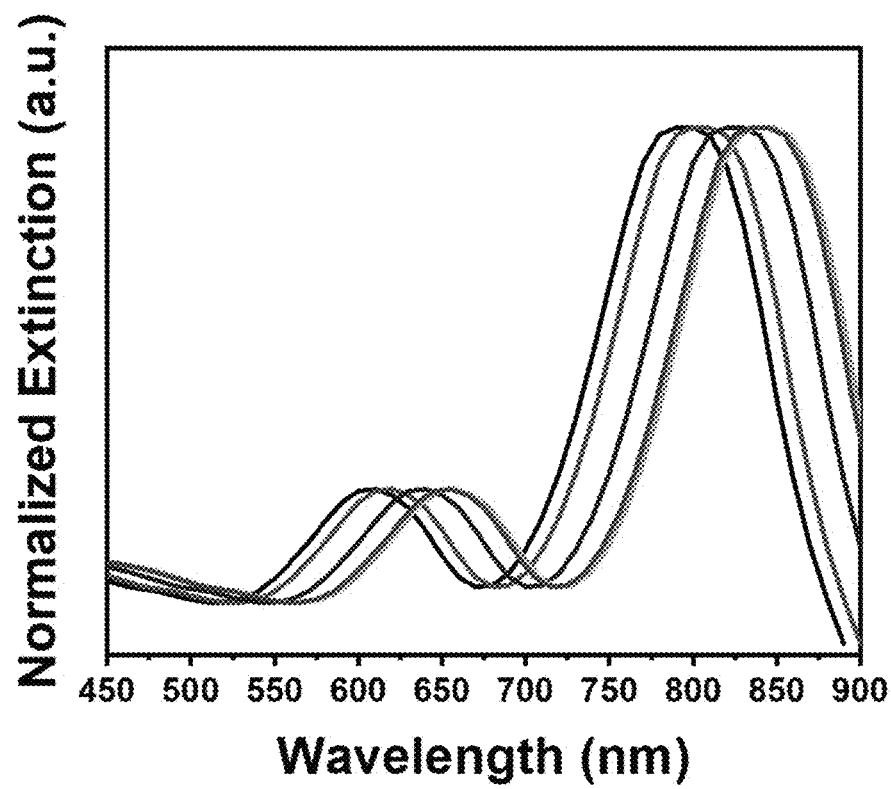
FIG. 13 shows the spectral changes of Au TNPs functionalization for test strip to capture the antibody/modified ssDNA. Accordingly, the LSPR peak position was obtained at 80 nm black line in acetonitrile and 810 nm red line in water. Upon PEGylated in solution phase average 23 nm red shift was observed (blue line). Then functionalized with antibody NMP22 average 18 nm further redshift was observed (green line) and when it functionalized with modified ssDNA 10b only 15 nm LSPR peak red shift was observed-Purple line (later shifts compare to LSPR peak of after PEGylating Au SPs).
Figure 14:
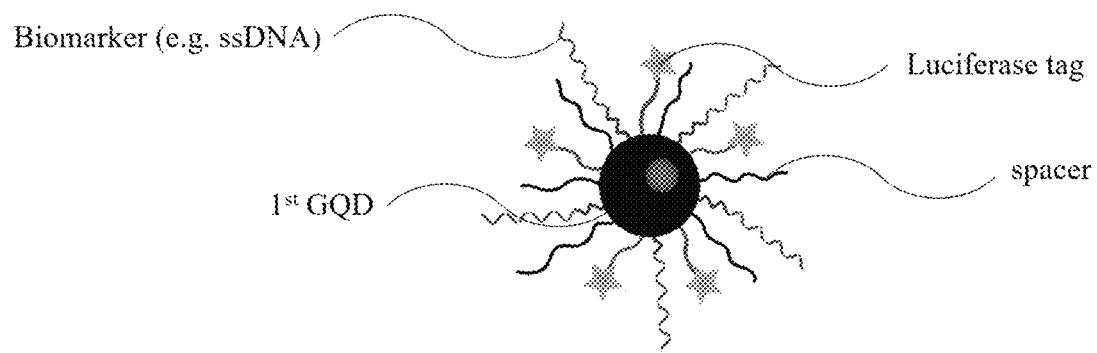
FIG. 14 and FIG. 15 are schematic views of some examples of a $1^{st}$ GQD contained in a second region/conjugate pad of the test strip shown in FIG. 1.
Figure 15:
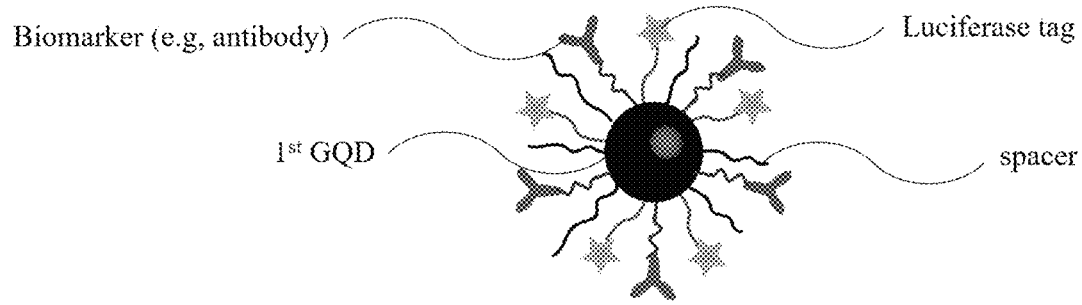

Here, we first started with Au Spherical particles and as shown in FIG. 11 we functionalized it with PEG-SH and then followed with the functionalization with either anti body for NMP22 (NO 9) or modified sequence to capture microRNA 10b conjugations (NO 3). The resulted conjugates were NO 24 and No 26 respectively. LSPR peak shifts were showed in FIG. 12 and Table 4 explains the summary of obtained shifts. Similar experiments were reported to obtained NO: 30 and NO: 32 using gold triangular nanoprisms and obtained LSPR shifts is shown and summarized on the FIG. 13 and Table 5, respectively.

TABLE 4

| Type of functional group | Absorption peak position (nm) | Peak shift (nm) |
|---|---|---|
| Au SPs in Water | 530 | |
| Au SPs in Water + PEG$_8$Acid | 543 | 13 nm |
| Au SPs in Water + PEG$_8$Acid + NMP Antibody (NO 9) | 553 | 10 nm |
| Au SPs in Water + PEG$_8$Acid + modified sequence for ssDNA10b (NO 3) | 551 | 8 nm |

TABLE 5

| Type of functional group | Absorption peak position (nm) | Peak shift (nm) |
| --- | --- | --- |
| Au TNPs in Acetonitrile | 800 | |
| Au TNPs in Water | 810 | 10 nm |
| Au TNPs in Water + PEG$_8$Acid | 833 | 23 nm |
| Au TNPs in Water + PEG$_8$Acid + NMP Antibody (NO 9) | 851 | 18 nm |
| Au TNPs in Water + PEG$_8$Acid + modified ssDNA10b (NO 3) | 848 | 15 nm |

Synthesis of Gold Spherical Nanoparticles (Au SNPs).

Figure 32:
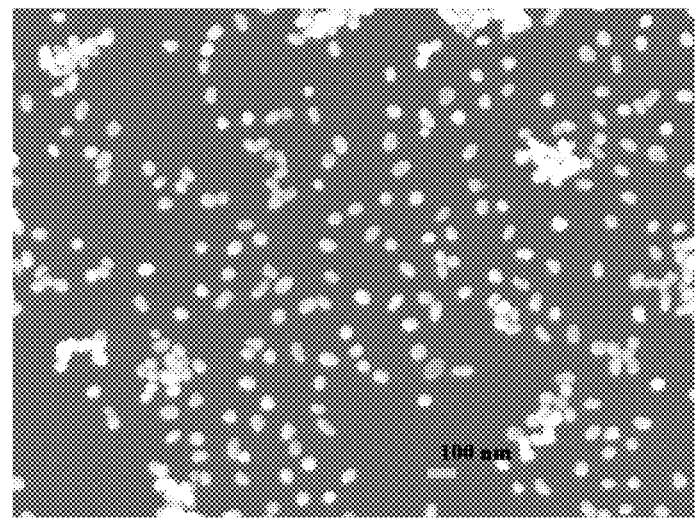
FIGS. 32 and 33 show the scanning electron microscopy obtained for the synthesized gold triangular nanoprisms and gold spherical particles. Scale bar indicated inside the image. All calibration plots were prepared in human urine
Figure 33:
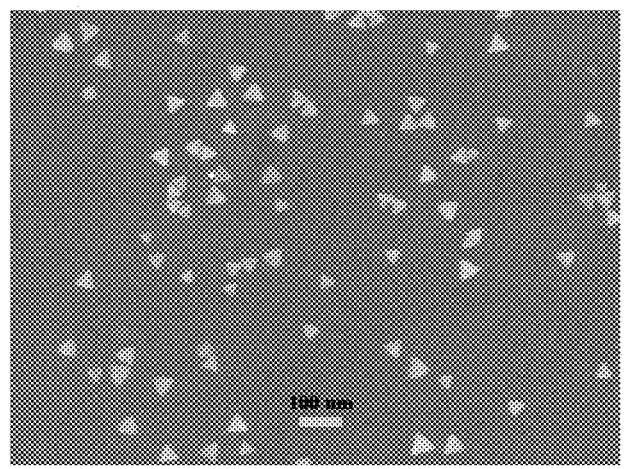

Au SNPs were prepared using some modification with literature published method. Accordingly, freshly prepared A 10 mL HAuCl4 H$_2$O solution with 4 mg/mL concentration was added to 390 mL in a 1 L Erlenmeyer flask and placed on a hot plate. Then solution temperature was gradually increased to boiling while vigorous stirring. Let the solution to vigorously boil for 5 minutes and then 3 mL aqueous solution of sodium citrate with 10 mg/mL concentration was injected to the solution. Let the reaction to continue the hot plate for another five minutes where the color changes of color less, yellow, yellow brown, brown, dark brown, and finally wine red was observed. At this point flask was taken away from the hot plate and left to come to room temperature. Lastly, the flask was lightly lidded and stored in the refrigerator for overnight before use. The SEM image of the synthesized Au SNPs is given at FIG. 32.

Functionalization of Gold Spherical Nanoparticles (Au SNPs) with Antibody.

Aqueous solution of citrate capped Au SNP (0.5 mg/mL) was mixed with SDS (0.025%) and PEGS acid (0.1 mg/mL) under basic conditions for overnight and then purification by centrifugation 13400 rpm for 30 minutes. Then separated PEGylated Au SNPs dissolved in 10 mM MES buffer at pH 5 and subjected to EDC/NHS functionalization using mixture of 10 mg/mL EDC and 100 mg/mL NHS and the resulted solution was left at 37° C. and 650 rpm for 30 min on orbit shaker for to activate the carboxylic groups of the PEGylated AuNPs. After the incubation, the excess of EDC-Sulfo-NHS was eliminated by centrifuging the solution in Amicon Ultra 0.5 filters (14 000 rpm; cut off, 50 K) for 5 min. After carboxylic activated on PEGylated Au SNPs for the antibody functionalization 40 μg/mL of antibody (e.g. ID NO: 9) were incubated in the MES buffer for 3 hrs at at 37° C. and 650 rpm on an orbit shaker. The obtained conjugates were centrifuged at 14 000 rpm at 4° C. for 20 min and then washed with 500 μL of bicarbonate buffer (10 mM, pH 7.5). Finally, the resulting oriented antibody/AuNP conjugates were resuspended in PBS buffer. Similarly for the ssDNA functionalization, After carboxylic activated on PEGylated Au SNPs 40 μg/mL of ssDNA with NH$_2$ linker (NO: 1) were incubated in the MES buffer for 3 hrs at 37° C. and 650 rpm on a orbit shaker. The obtained ssDNA-Au NPs conjugates were centrifuged at 14 000 rpm at 4° C. for 20 min and then washed with 500 μL of bicarbonate buffer (10 mM, pH 8). Finally, the resulting oriented antibody/AuNP conjugates were resuspended in PBS buffer. All the functionalization step LSPR peak changes showed in FIG. 12.

Synthesis of Gold Triangular Nanoprisms:

Gold nanoprisms were chemically synthesized according literature reported method and Accordingly, 40 mL of acetonitrile was measured to the Erlenmeyer flask and 18 mg of Et3PAu(I)Cl 18 mg was dissolved in the acetonitrile and stir at 150 rpm until dissolved. Then 36 μL of TEA was added to the mixture and reaction was heated internal temperature to reach 38-40° C. and once temperature is reached 600 μL of PMHS were injected to the solution and maintain the temperature at 40° C. where within 3 hours reaction color changed from colorless to pink, purple, blue and back to bluish purple which indicating the formation of nanoprisms with a stable absorbance dipole peak at 800 nm in acetonitrile. The solution was then removed from heat, centrifuged at 4000 rpm for 2 minutes to remove excess untreated PMHS.

Solution Phase PEG Functionalization of the Synthesized Au TNPs and EDC/NHS Coupling with Antibody/Complimentary ssDNA-NH$_2$.

After centrifugation, the supernatant was carefully transferred to new centrifuge tubes and centrifuged at 10,000 rpm for 30 minutes to precipitate out all the synthesized nanoprisms. Then redissolved in 10 mL nanopure water and added SDS (0.025%) and PEGS acid (0.1 mg/mL) under basic conditions for overnight on an orbit shaker. Next day PEGylated Au TNPs were subjected to continuous precipitation purification to separate the 42 nm Au TNPs with no truncated structures. Accordingly, continuous precipitation at 5000 rpm for 1 min, 2 min, 3 min and 7 min carried out and at 7 minutes precipitation 42 nm Au TNPs were separated with no truncated structures and confirmed using SEM. 0.5 mg/mL purified PEGylated Au TNPs dissolved in 10 mM MES buffer at pH 5 and subjected to EDC/NHS functionalization using mixture of 10 mg/mL EDC and 100 mg/mL NHS and the resulted solution was left at 37° C. and 650 rpm for 30 min on orbit shaker to activate the carboxylic groups of the PEGylated AuNPs. After the incubation, the excess of EDC-Sulfo-NHS was eliminated by centrifuging the solution in Amicon Ultra 0.5 filters (14 000 rpm; cut off, 50 K) for 5 min. After carboxylic activated on PEGylated Au TNPs for the antibody functionalization 40 μg/mL of antibody (e.g. ID NO: 9) were incubated in the MES buffer for 3 hrs at 37° C. and 650 rpm on an orbit shaker. The obtained conjugates were centrifuged at 14 000 rpm at 4° C. for 20 min and then washed with bicarbonate buffer (10 mM, pH 7.5). Finally, the resulting oriented antibody/Au TNP conjugates were resuspended in PBS buffer. Similarly for the ssDNA functionalization was carried out, After carboxylic activated on PEGylated Au SNPs 40 μg/mL of ssDNA with NH$_2$ (e.g.: NO: 1) were incubated in the MES buffer for 3 hrs at 37° C. and 650 rpm on an orbit shaker. The obtained ssDNA-Au NPs conjugates were centrifuged at 14 000 rpm at 4° C. for 20 min and then washed with bicarbonate buffer (10 mM, pH 8). Finally, the resulting oriented antibody/AuNP conjugates were resuspended in PBS buffer. All the functionalization steps were monitored using LSPR peak changes showed in FIG. 13.

Designing the Lateral Flow Assay

Conjugate Pad Selection and Pretreatment and Preparation

Typically, the material in which conjugate pads are made are either glass fiber or cellulose filter. Cellulose filters typically have higher volume retention than glass fiber. A slow release rate was expected for the urine based assay and we need to make sure it has the capability of larger volume of conjugate for six different test strips and release the conjugate slowly which allowed more time for the conjugation with the target analyte. Accordingly, after several optimization we have selected STANDARD14 material for our sensor development. After the selection of conjugate pad, it was subjected for the pretreatment using borate running buffer with 20% sucrose. Then manually dispense the mixture of GQDs separately as mentioned in Table 6 and after dispensing the conjugates, all prepared conjugates pads were then dried in a forced-air convection oven for 1 hour at 37° C. The dried conjugate pads are then cured overnight in a desiccated environment with <20% humidity prior to testing.

TABLE 6

| Conjugate Pad composition | Identity |
|---|---|
| GQDs + Luc + anti NMP22 antibody (NO 9) | NO: 16 |
| GQDs + Luc + anti BTA antibody (NO 11) | NO: 17 |
| GQDs + PEG$_8$Acid + modified ssDNA10b (NO 1) | NO: 18 |
| GQDs + PEG$_8$Acid + modified ssDNA 145 (NO 4) | NO: 19 |
| GQDs + PEG$_8$Acid + Luciferase + modified ssDNA UCA 1 (NO 6) | NO: 20 |
| GQDs + PEG$_8$Acid + Luciferase + anti IgG antibody (NO 14) | NO: 21 |
| Mixture of SEQ ID NO: 16 + SEQ ID NO: 17 + NO: 18 + NO: 19 + NO: 20 + NO: 21 | NO: 22 |

Nitrocellulose Membrane Selection Pretreatment and Preparation

To improve assay performance, we optimized the membrane selection using wide range of membranes and found FF170HP nitrocellulose membrane ideal for the assay based on its low viscosity samples with a flow rate of 156 s/4 cm. The receptor binding capacity to the membrane is very important for the assay development and therefore we used striping of the test and control lines onto nitrocellulose membranes using (ALFRD) lateral flow reagent dispenser & std accessories and Fusion 200 Syringe Pump. Accordingly, we used 0.2 mL/min dispensing rate with 4.5V and as a result we obtained more uniform ~1 mm thickness lines.

We prepared series of nitrocellulose membranes as summarized in Table 7 and each combination were used to build up the calibration curves. Table 8 shows the summary of all Sequential IDs used for the study. The nucleotide sequences as provided when needed.

TABLE 7

| Membrane functionalization | Identity |
|---|---|
| Au SPs + PEG8 Acid + anti NMP22 (NO: 9) | NO: 23 |
| Au SPs + PEG8 Acid + anti BTA antibody (NO: 11) | NO: 24 |
| Au SPs + PEG8 Acid + CCCCCCCCCCCCC-NH$_2$ (For microRNA10b) | NO: 25 |
| Au SPs + PEG8 Acid + GGGGGGGGGGGGG-NH$_2$ (For microRNA 145) | NO: 26 |
| Au SPs + PEG8 Acid + AAAAAAAAAAAA-NH$_2$ For UCA | NO: 27 |
| Au TNPs + PEG8 Acid + anti NMP2 (NO: 9) | NO: 28 |
| Au TNPs + PEG8 Acid + anti BTA antibody (NO: 11) | NO: 29 |
| Au TNPs + PEG8 Acid + CCCCCCCCCCCCC-NH$_2$ (For microRNA10b) | NO: 30 |
| Au TNPs + PEG8 Acid + GGGGGGGGGGGGG-NH$_2$ (For microRNA 145) | NO: 31 |
| Au TNPs + PEG8 Acid + AAAAAAAAAAAA-NH$_2$ For UCA | NO: 32 |
| Au TNPs + PEG8 Acid + IgG (NO 15) | NO: 33 |
| Mixture of NO: 28 + NO: 29 + NO: 30 + NO: 31 + NO: 32 + NO: 33 | NO: 34 |

TABLE 8

| Receptor and Analytes | Sequences | Identity |
|---|---|---|
| Modified 10b ssDNA | 5' NH$_2$CAC AAA TTC GGT TCT ACA GGG TAGGGGGGGGGGGG 3' | SEQ ID 01 |
| MicroRNA 10b | 5' UACCCUGUAGAACCGAAUUGUG 3' | SEQ ID 02 |
| Modified 145 ssDNA | 5' AGGGATTCCTGG GAAAACTGGACCCCCCCCCCCC 3' | SEQ ID 03 |
| MicroRNA 145 | 5' GUCCAGUUUUCCCAGGAAUCCCU 3' | SEQ ID 04 |
| Modified ssDNA for UCA 1 | 3' CCGGGGTAATGTATCATCGGCTTAGCTCGAGCTAAGCCGA TGATACATTACCTTTTTGTTTTTTTTTTT5' | SEQ ID 05 |

TABLE 8-continued

| Receptor and Analytes | Sequences | Identity |
|---|---|---|
| UCA1 Long noncoding RNA 5'3' | 5'GGCCCCAUUACAUAGUAGCCGAAUCGAGCUCGAUUCGGCU ACUAUGUAAUGGAAAAAC3' | SEQ ID 06 |
| Test line sequence for ssDNA-10b | CCCCCCCCCCCC-NH2 | SEQ ID 07 |
| Test line sequence for ssDNA-145 | GGGGGGGGGGGG-NH2 | SEQ ID 08 |
| Test line sequence for UCA1 | AAAAAAAAAAAA-NH2 | SEQ ID 09 |

Developing Calibration Plots: Calibration Curve was Developed Using 100 nM, 10 Nm, 1 nM, 100 pM, 10 pM, 1 pM, 100 fM Concentrations Accordingly, for microRNA 10b-737.07 ng/mL to 7.37E-4 ng/mL solution was prepared For microRNA 145 671.22 ng/mL to 66.71E-4 ng/mL solution was prepared For LncRNA-UTA 1866.4 ng/mL to 1.864 E-3 ng/mL solution was prepared For NMP22 protein 3100 ng/mL to 0.003 ng/mL solution was prepared For BTA protein 7703 ng/mL to 0.007 ng/mL solution was prepared For the Assay development Whatman FF170HP nitrocellulose membrane (GE Healthcare) was assembled on an adhesive backing card (MIBA-020; DCN Diagnostics) with Whatman standard 14 pretreated sample pad and Whatman standard 14 pretreated and prepared conjugate pad and Whatman CF 5 absorbent pad. The resulting master sheet, using a guillotine cutter, cut the received test strips 3.3 mm wide. Test strips together with a desiccant (0.6 g of silica gel in bags) were sealed in a plastic foil pact and store in the fridge.

200 μL of a sample containing specific analyte (NO: 2,5,7,10,12) separately with above mentioned dilution range and mixture of those analytes in the above mentioned dilution range were prepared in human urine to a Eppendorf tube and 5 μL of 20% Tween 20 were added to each tubes. Then 220 μL of sample solution were added to the conjugate pads for target test cartridge as mentioned in Table 6. And due to the capillary action sample was moving to the conjugate pad and A test strip was immersed into the sample for 7 min. Then the test strip was transferred into a running buffer and left for 3 minutes. After this, the test strip was immersed into the Luciferase Assay Buffer (contains 500 mM MgCl$_2$, 400 mM Tris-HCl, pH 7.8, 25 mM CoA, 200 mM ATP, 10% Triton-X-100 and D-Luciferin 10 mM) and recorded the luminescent intensity using newly developed technology where we used the camera on an iPhone 5S smartphone that is coupled to luminescent lateral flow reader is based on the scanning approach without using any moving components or any extra optical accessories. Instead, the test line and the area around it, are scanned using CMOS Image Sensor (CIS), specifically designed for this application and the proprietary of this design will be claimed separately. The obtained Smartphone camera-based image followed by an application based on Image J software termed IJ_mobile to calculate the intensity of the bands in relative light intensity units (RLU) and these values were plotted using origin pro software in order to obtain the LOD of the assay. The data was normalized by subtracting the value obtained in the blank (The intensity obtained for the metal nanoparticles captured test strips), and the achieved LOD are summarized in Table 9 and Table 10 reported the all obtain RLU for each concentrations.

TABLE 9

| Conjugate Pad ID | Target Analyte | Test strip composition | Equation and $R^2$ | Calculated LOD fg/mL |
|---|---|---|---|---|
| NO: 16 | NO: 10 | NO: 23 | y = 964.57ln(x) + 7520<br>$R^2$ = 0.995 | 1035 |
| NO: 16 | -NO: 10 | NO: 28 | y = 970.74ln(x) + 9069.3<br>$R^2$ = 0.9804 | 92.9 |
| NO: 17 | NO: 12 | NO: 24 | y = 1060.5ln(x) + 7267.8<br>$R^2$ = 0.9795 | 928 |
| NO: 17 | NO: 12 | NO: 29 | y = 1027.8ln(x) + 8550<br>$R^2$ = 0.9764 | 25.7 |
| NO: 18 | NO: 2 | NO: 25 | y = 899.11ln(x) + 6762.6<br>$R^2$ = 0.9977 | 1039 |
| NO: 18 | NO: 2 | NO: 30 | y = 1131.9ln(x) + 10063<br>$R^2$ = 0.9936 | 14.48 |
| NO: 19 | NO: 5 | NO: 26 | y = 911.81ln(x) + 7556.3<br>$R^2$ = 0.9985 | 1120 |
| NO: 19 | NO: 5 | NO: 31 | y = 989.55ln(x) + 10141<br>$R^2$ = 0.9961 | 37.52 |
| NO: 20 | NO: 7 | NO: 27 | y = 989.45ln(x) + 4418.1<br>$R^2$ = 0.9996 | 1925 |
| NO: 20 | NO: 7 | NO: 32 | y = 1055.8ln(x) + 7925.7<br>$R^2$ = 0.9803 | 580 |

TABLE 10

| SEQ ID NO: 10 | Concentration mol/L | Concentration ng/mL | RLU on NO: 23 | STD on NO: 23 | RLU on NO: 28 | STD on NO: 28 |
|---|---|---|---|---|---|---|
| | 1.00E+02 | 3100 | 15420 | 528 | 17932 | 532 |
| | 1.00E+01 | 310 | 13274 | 697 | 14987 | 935 |
| | 1.00E+00 | 31 | 10925 | 872 | 11652 | 445 |

TABLE 10-continued

|  |  |  |  |  |  |
|---|---|---|---|---|---|
| 0.1 | 3.1 | 7965 | 648 | 9425 | 785 |
| 0.01 | 0.31 | 6120 | 789 | 7214 | 987 |
| 0.001 | 0.031 | 4300 | 1021 | 5128 | 1025 |
| 1.00E−04 | 0.0031 | 2275 | 935 | 3975 | 879 |
| 1.00E−05 | 0.00031 |  |  | 2087 | 989 |

| SEQ ID NO: 12 | Concentration mol/L | Concentration ng/mL | RLU on NO: 24 | STD on NO: 24 | RLU on NO: 29 | STD on NO: 29 |
|---|---|---|---|---|---|---|
|  | 1.00E+02 | 7703 | 14800 | 428 | 18032 | 875 |
|  | 1.00E+01 | 770 | 12375 | 532 | 15687 | 786 |
|  | 1.00E+00 | 70 | 9687 | 782 | 12384 | 597 |
|  | 0.1 | 7 | 7842 | 795 | 9425 | 875 |
|  | 0.01 | 0.7 | 6320 | 879 | 6852 | 789 |
|  | 0.001 | 0.07 | 4128 | 920 | 4200 | 922 |
|  | 1.00E−04 | 0.007 | 2220 | 883 | 3600 | 728 |
|  | 1.00E−05 | 7E−4 |  |  | 2120 | 1035 |

| SEQ ID NO: 2 | Concentration mol/L | Concentration ng/mL | RLU on NO: 25 | STD on NO: 25 | RLU on NO: 30 | STD on NO: 30 |
|---|---|---|---|---|---|---|
|  | 1.00E+02 | 737.07 | 12420 | 575 | 17200 | 583 |
|  | 1.00E+01 | 73.7 | 10800 | 625 | 15800 | 786 |
|  | 1.00E+00 | 7.37 | 8770 | 790 | 11900 | 584 |
|  | 0.1 | 0.737 | 6520 | 575 | 9720 | 678 |
|  | 0.01 | 0.0737 | 4430 | 820 | 6875 | 1058 |
|  | 0.001 | 0.00737 | 2200 | 1075 | 4325 | 958 |
|  | 1.00E−04 | 7.37E−04 |  | 928 | 2200 | 972 |

| SEQ ID NO: 5 | Concentration mol/L | Concentration ng/mL | RLU on NO: 26 | STD on NO: 26 | RLU on NO: 31 | STD on NO: 31 |
|---|---|---|---|---|---|---|
|  | 1.00E+02 | 671.22 | 13620 | 583 | 16275 | 625 |
|  | 1.00E+01 | 67.122 | 11275 | 575 | 14200 | 582 |
|  | 1.00E+00 | 6.7122 | 9100 | 695 | 12654 | 720 |
|  | 0.1 | 0.67122 | 7320 | 872 | 9870 | 578 |
|  | 0.01 | 0.06712 | 5240 | 928 | 7254 | 972 |
|  | 0.001 | 0.00671 | 2900 | 935 | 5100 | 953 |
|  | 1.00E−04 | 6.71E-4 |  |  | 2875 | 1027 |

| SEQ ID NO: 7 | Concentration mol/L | Concentration ng/mL | RLU on NO: 27 | STD on NO: 27 | RLU on NO: 32 | STD on NO: 32 |
|---|---|---|---|---|---|---|
|  | 1.00E+02 | 1866.4 | 11825 | 828 | 15122 | 925 |
|  | 1.00E+01 | 186.64 | 9685 | 765 | 13958 | 698 |
|  | 1.00E+00 | 18.664 | 7232 | 898 | 11475 | 545 |
|  | 0.1 | 1.8664 | 5102 | 1031 | 8420 | 538 |
|  | 0.01 | 0.18664 | 2725 | 793 | 6836 | 725 |
|  | 0.001 | 0.01864 |  | 785 | 2988 | 988 |

Figure 34A:
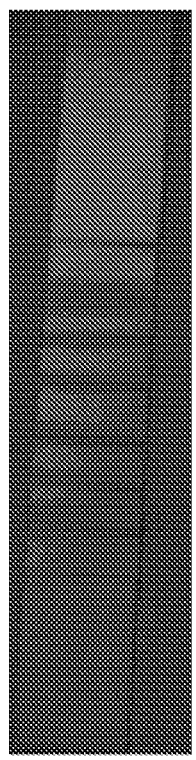
FIG. 34A shows the photograph of the LSPR test strip with six analytes and FIG. 34B represents the color imaged observed from the CMOS Image Sensor (CIS).
Figure 34B:
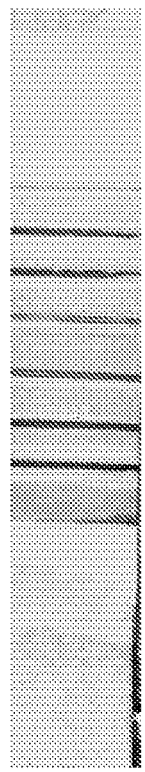

Once we obtained the individual test strips then our challenged was to detect all the six analytes in a one assay (including control line). As shown in the FIG. 34A and FIG. 34B we developed the sensing platform with functionalized gold triangular nanoprisms to capture the conjugates that contained as mentioned in NO: 22 conjugates. Accordingly, we introduced 1:1:1:1:1:1 all Numbers explained in SEQ ID NO: 22 and prepared the conjugation pad similarly in the method we explained in section 0028. Then the test strips were prepared as explained in the NO: 34 by following in the experimental procedure on 0029. Half test strip method carried out to see the intensity of the test line by using 200 µL of a sample in urine with 1 nM concentration of mixture of NO: 2,5,7,10,12,15. (each analyte was obtained with 1 nM concentration in the mixture). The test strip was run for approximately 20 minutes and obtained color intensities were summarized in the Table 11 and FIG. 34A shows the photograph of the LSPR test strip with six analytes. FIG. 34B represents the color imaged observed from the CMOS Image Sensor (CIS).

The obtained intensities were almost aligned with the intensities we observed in the individual calibration curve.

TABLE 11

| NO: 21 | Concentration mol/L | NO: 34 | RLU on | STD |
|---|---|---|---|---|
| NO: 16 | 1.00E+00 | NO: 28 | 11208 | 945 |
| NO: 17 | 1.00E+00 | NO: 29 | 11087 | 1025 |
| NO: 18 | 1.00E+00 | NO: 30 | 11432 | 745 |
| NO: 19 | 1.00E+00 | NO: 31 | 11875 | 1025 |
| NO: 20 | 1.00E+00 | NO: 32 | 10987 | 875 |
| NO: 21 | 1.00E+00 | NO: 33 | 11231 | 1035 |

To facilitate a better understanding of the present invention, specific terms are defined in the present invention for convenience. Unless particularly defined otherwise, scientific, and technical terms used herein have meanings generally understood by those of ordinary skill in the art. In addition, it should be understood that, unless particularly indicated in the context, the singular forms include plural forms thereof, and the plural terms also include singular forms thereof.

Hereinafter, a test kit for detecting an analyte in a bodily fluid sample according to the present invention and at home point-of-care system comprising the same will be described in further detail.

According to the present invention, a test kit and system for detecting an analyte in a bodily fluid sample is provided.

FIG. 1 is the schematic view of a test strip of the kit according to an embodiment of the present invention.

(then (Referring to FIG. 1, a biosensor(100) for detecting of an analyte in a bodily fluid sample according to an embodiment of the present invention comprises i) a first region (110), wherein the bodily fluid sample is housed; ii) a second region (120), positioned downstream of the first region (110), wherein the bodily fluid sample housed in the first region (110) is moved by the lateral flow capillary action; iii) a third region (130) positioned downstream of the second region (120), wherein the GQD to which the analyte is bound and/or the GQD to which the analyte is not bound are moved by the lateral flow capillary action; and iv) a fourth region (140) positioned downstream of the third region (130), wherein all unbound GQD and excess the bodily fluid sample is absorbed.

In addition, if the test strip is inserted into a system that reads test strip intensity in the designed luminometer intensity of each test region reads and transferred to a smartphone app to convert to the concentration profile. Further connected to a cloud-based database to statistically analyses the biomarkers correlation for the specific disease for identification of disease stage vs healthy individuals.

In this embodiment of the first region (110) is a sample pad region in which the bodily fluid sample is introduced into the test strip. The bodily fluid sample that can be analyzed by the test strip includes at least one selected from whole blood, human plasma, bovine plasma, phosphate buffered saline, water, serum, saliva, urine, tears, pancreatic juice, bile juice, saliva, peritoneal fluid, gastric juice, digestive juice, bone marrow, cerebrospinal fluid, stools, semen, vaginal fluid, mucosa and fluid extracted from tissue, but is not necessarily limited thereto.

The bodily fluid sample may or may not include a target analyte of the test kit according to the present invention. The test strip according to the present invention will generate a detectable signal via at least one biological and/or chemical reaction only if the analyte is contained in the bodily fluid sample.

The analyte can be a variety of forms of DNA and RNA (e.g. micro RNA, long non-coding RNA) or proteins (e.g., antigens) contained in the bodily fluid sample, but is not necessarily limited thereto. In other words, the analyte is to be understood as a substance contained in the bodily fluid sample and detectable through at least one biological and/or chemical reaction. For example, the analyte may be a substance that can be detected by complementary binding between RNA sequences or an antigen-antibody immune response of proteins.

Furthermore, the bodily fluid sample may be a fluid itself such as blood, plasma, serum, saliva, urine, tears, gastric juice, digestive juice, bone marrow, cerebrospinal fluid, stools, semen, vaginal fluid and a fluid extracted from tissue, output of post-treatment of the fluid (e.g., reagent treatment or centrifugation etc.), or a mixture of the fluid itself or the output of post-treatment and other fluid (e.g., distilled water, saline, etc.).

The bodily fluid sample introduced into the first region (110) can be moved from the first region (110) in the test strip (100) ultimately to a fourth region (140) in the test strip (100) by lateral flow capillary action.

First, the bodily fluid sample compartment in the region (110) moves to the second region (120) that is positioned downstream of the first region (110) by lateral flow capillary action.

The second region (120) is a conjugate pad region that induces the binding of the analyte and GQD of the biological fluid sample moved from the first region (110) by side flow capillary action and converts the analyte to a detectable form.

The second region (120) may contain GQDs mixture including at least one GQD specific to at least one analyte of the biological fluid sample or specifically functionalized for control stripe in the third region. the diameter of the GQD is between 5 nm to 100 nm, and the GQD appears the UV-vis spectrum the range of 350 nm to 750 nm.

More specifically, the GQDs mixture may contain i) a $1^{st}$ GQD with a luciferase protein tag, and an ssDNA and/or antibody specific for at least one analyte (microRNA, lnc RNAs or proteins) attached to the surface; and ii) a $2^{nd}$ GQD with a luciferase protein tag and IgG antibody attached to the surface. Here, GQDs forming core of the $1^{st}$ GQD and the $2^{nd}$ GQD mean graphene-based quantum dots in the form of particles in nanometers (nm).

Figure 2:
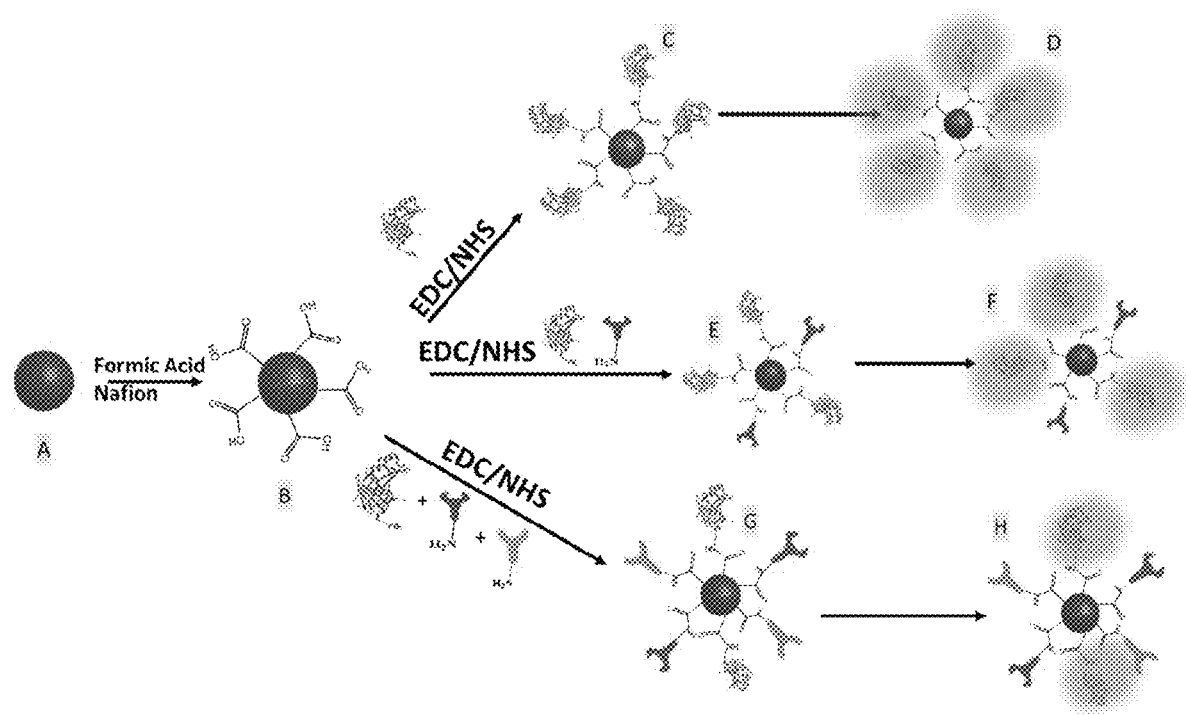
FIG. 2 shows the functionalization scheme of graphene quantum dots with formic acid for the preparation of protein capturing platform and subsequent functionalization plan for the optimization.
Figure 3:
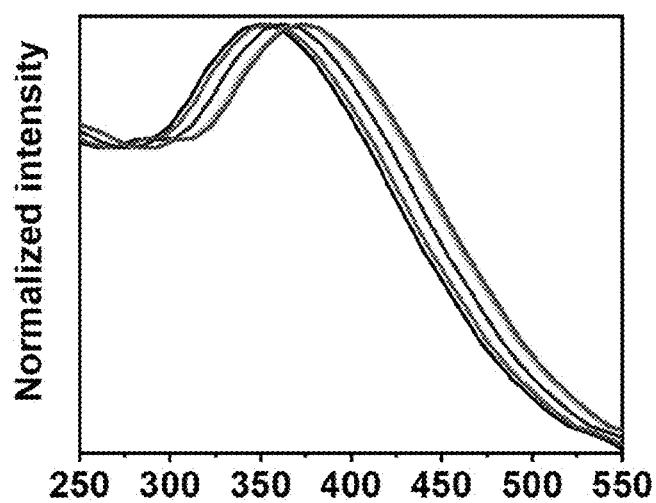
FIG. 3 shows the Absorbance peak changes upon binding with different functionalization steps. Accordingly, GQDs shows absorbance peak appeared at 350 nm and after functionalizing with acetic acid it has red shifted 3 nm. Upon functionalizing with luciferase or luciferase and NMP22antibody or Luciferase, NMPP22 antibody and biotin has given 8 nm, 12 nm and 14 nm red shifting, respectively.
Figure 4:
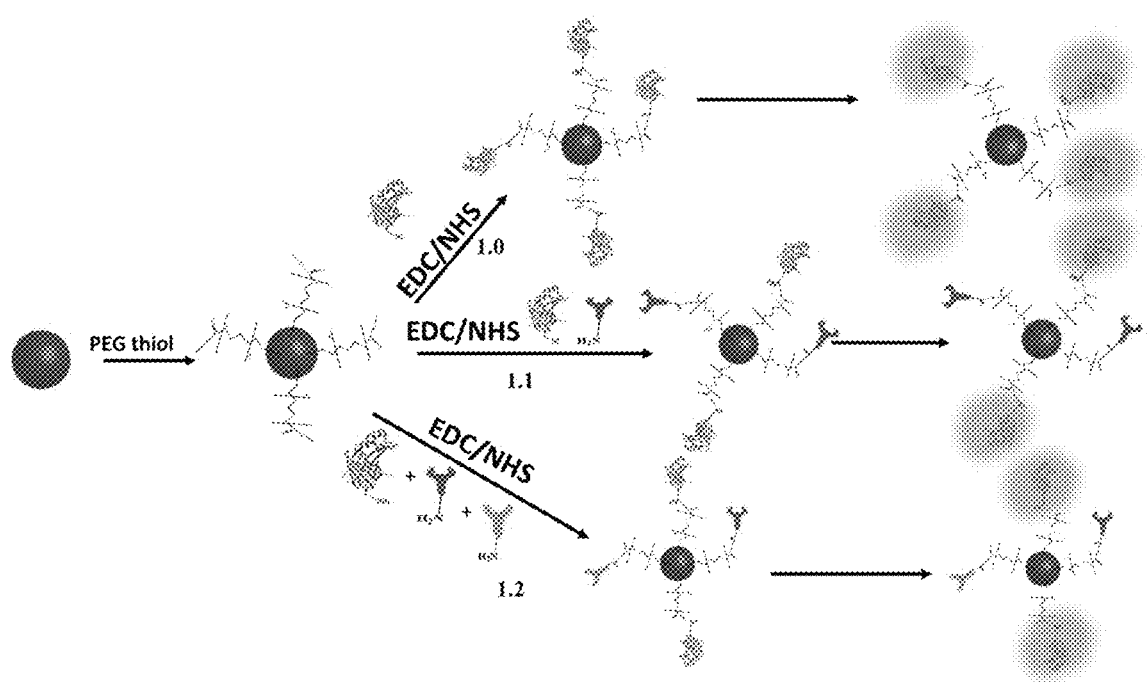
FIG. 4 shows the functionalization scheme of graphene quantum dots with $PEG_8SH$ acid for the preparation of protein capturing platform and subsequent functionalization plan for the optimization.
Figure 5:
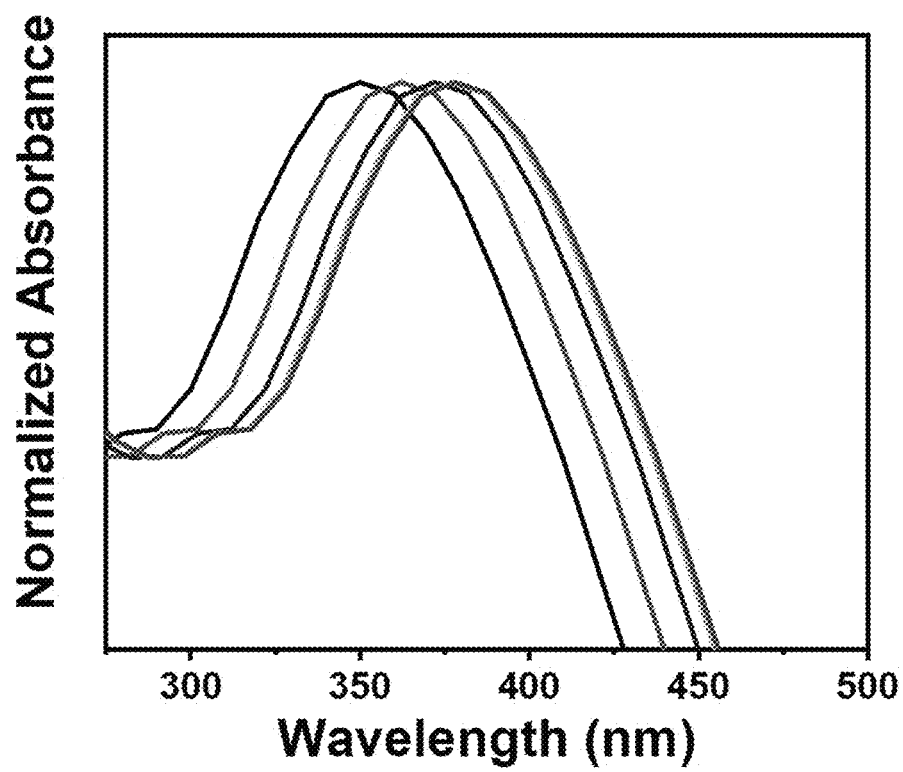
FIG. 5 shows the Absorbance peak changes upon binding with different functionalization steps. Accordingly, GQDs shows absorbance peak appeared at 350 nm and after functionalizing with $PEG_8$ acid it has red shifted 12 nm. Upon functionalizing with luciferase or luciferase and NMP22antibody (1:1) or Luciferase, NMPP22 antibody and biotin (1:1:1) has given 10 nm, 15 nm and 16 nm red shifting, from the $PEG_8$ acid peak position, respectively.

FIG. 2 and FIG. 3 are schematic views of some examples of a $1^{st}$ GQD included in the second region (120) of the biosensor shown in FIG. 1, and FIG. 4 and FIG. 5 are schematic views of an analyte is bound to the $1^{st}$ GQD shown in FIG. 2 and FIG. 3, respectively.

Referring to FIG. 2 and FIG. 3, a biomarker such as ssDNA and/or antibody specific to the analyte may be selectively attached to the surface of the $1^{st}$ GQD depending on the type of the target analyte.

On the surface of $1^{st}$ GQD, the $1^{st}$ GQD has the ssDNA has complementary nucleotide sequences capable of binding to a target ssDNA in the analyte or the antibody capable of binding to a target protein in the analyte by an antigen-antibody immune response.

For example, on the surface of $1^{st}$ GQD, a biomarker of ssDNA type can be attached, such as 5'-SH-C3-ssDNA-10b targeting microRNA 10b, 5'-SH-C3-ssDNA145 targeting microRNA 145, or ssDNA-C3-UCA targeting lncRNA UCA (see FIG. 2), or a biomarker of protein or antibody type can be attached such as NMP antibody targeting NMP proteins or BTA antibody targeting BTA proteins (see FIG. 3). [0042] As such, according to the type of a biomarker attached to the surface of the 1st GQD, the types of a disease detectable by the biosensor may vary.

As such, according to the type of a biomarker attached to the surface of the 1st GQD, the types of a disease detectable by the test strip may vary. Similarly, for two diseases simultaneous diagnosis same structure but different biomarkers and biomarker receptor is used.

In certain aspects, the microRNA of interest can be a member of the let 7 miR family, -5p miRs, miR-3p miRs, edited miRs, loop miRs, and the like. In certain aspects, the miR of interest can be miR-7, miR-7-2, miR-7-2*, miR-9*, miR10a, miR-10b, miR-15a, miR-15b, miR-16, miR16-1, miR-16-2, miR-17, miR-18a, miR-18b, miR-19a, miR-19a*, miR-19b* miR-19b, miR-19b2, miR-20a, miR-20b, miR-21, miR-21*, miR-22, miR-22-3p, miR-23a, miR-23a*, miR-24, miR24*,miR-24-2*, miR-25, miR-25*, miR-26a, miR-26b, miR-27a, miR-27a*, miR-27b, miR-27b*, miR-28, miR-28-3p, miR-29a, miR-29a*, miR-29b, miR-29c, miR-29c*, miR-30a*, miR-30a-3p, miR-30a-5p, miR-30b, miR-30c, miR-30c-1, miR-30c-2, miR30d, miR-30e, miR-30e*, miR-31, miR-31*, miR-32, miR-33a, miR-33a*, miR-33aloop, miR-34a, miR-34b*, miR-34a-loop, miR34c-5p, miR-92a, miR-92a*, miR-92b, miR-92b*, miR-93, miR-93* miR-95, miR-96, miR-99a, miR-99b, miR-99b*, miR100, miR-100*, miR-101, miR-101*, miR-103, miR-103a, miR-106a, miR-106b, miR-106b*, miR-107, miR-122, miR-124, miR-124*, miR-125a, miR-125b, miR125b-1, miR-125b-2, miR-126, miR-126*, miR-128, miR-129-1, miR-129-2, miR-129-3p, miR129-5p, miR-130a, miR-130b, miR-130b*, miR-132, miR-133a, miR-133a*, miR-133b, miR134, miR-135b, miR-135b*, miR-136, miR-136*, miR139, miR-140, miR-140-3p, miR-141, miR-141*, miR-142, miR-142-3p, miR-143, miR-143*, miR-144*, miR-145, miR-146a, miR147, miR-147b, miR-148a, miR148a*, miR-148b, miR-148b*, miR-150, miR-151, miR-153, miR-154, miR-154*, miR-155, miR-181a, miR-181a*, miR-181a-2, miR-181a-2*, miR-181b, miR-181c, miR-182, miR-183, miR-184, miR-185, miR-186, miR-187, miR-190, miR-190a, miR-190b, miR-191, miR-192, miR-192-loop, miR-193b, miR-193b*, miR-193b-3p, miR-194, miR-194* miR-195, miR-196, miR-196a, miR-196b, miR-198, miR-199a3p, miR-199a-5p, miR199b-3p, miR-199b-5p, miR-200a, miR-200b, miR-200c, miR-200c*, miR-203, miR-204, miR205, miR-208, miR-210, miR-212, miR-215, miR-216, miR-216a, miR-216b, miR-217, miR-218-1, miR-218-2, miR-219-1-3p, miR-219-2, miR-219-3p, miR-219-5p, miR-219-loop, miR-219-2-loop, miR-221, miR-222, miR-222*, miR-223, miR-223*, miR-301a, miR-320a, miR-320b, miR320b*, miR-323-3p, miR-324, miR-324-3p, miR-330-5p, miR-331, miR-331-3p, miR-335, miR337-3p, miR-338-5p, miR-339, miR-340, miR-342, miR-342-3p, miR342-5p, miR-345, miR 361, miR-362, miR-362-3p, miR-363, miR-365, miR-369*, miR-370, miR-373, miR-374a, miR-15-374a*, miR-375, miR-376a, miR-376a-1, miR-376b, miR-376c, miR-377, miR-377*, miR-379, miR-379*, miR-381, miR381*, miR-382, miR-383, miR-409*, miR-410*, miR-411, miR-411*, miR-421, miR-423-5p, miR-431, miR-432, miR-432*, miR-433, miR-449a, miR-449b, miR450b-5p, miR-451, miR-451a, miR-452, miR-454, miR-455, miR-455-3p, miR-484, miR-486, miR-486-3p, miR-486-5p, miR-487b, miR-490-3p, miR-492, miR-493*, miR-494, miR-497, miR-497*, miR-499-5p, miR-501*, miR-501-5p, miR505, miR-508-3p, miR-509-5p, miR-512-3p, miR-513-3p, miR-516a-1, miR-516a-2, miR-516a-3p, miR-516b-1, miR-518d-3p, miR-518e, miR-518f, miR-520 c-3p, miR-532, miR-539, miR-542*, miR-542-5p, miR-543, miR-548am, miR-548au, miR-548c, miR-548o, miR-548b-5p, miR-551b, miR-551b*, miR-552, miR-554, miR566, miR-571, miR-575, miR-582, miR-582-3p, miR-584, miR-589, miR-589*, miR-590-5p, miR-592, miR-598, miR-604, miR-605, miR-614, miR-615, miR-616, miR-616*, miR-622, miR-625, miR-627, miR-628-3p, miR-635, miR-636, miR-639, miR-640, miR-641, miR-642b, miR-642b-3p, miR-643, miR-644, miR-646, miR648, miR-649, miR-650, miR-652, miR-654*, miR-654-5p, miR-656, miR-672, miR-708, miR-711, miR-744*, miR-762, miR-766, miR-769-5p, miR-801, miR-874, miR-875-5p, miR-877, miR-885-5p, miR-886-5p, miR-888, miR-889, miR-889*, miR-891a, miR-922, miR-923, miR-935, miR-937, miR-939, miR-941, miR944, miR-1207, miR-1246, miR-1288, miR-1295, miR-1468, miR-1909, miR-2355, miR-2964a, miR 3125, miR-3154, miR-3177, miR-3184, miR-3188, miR-3605, miR-3942, miR-4253, miR-4286, miR-4529, miR-4646, miR-4653, miR-4666, miR-4667, miR-4697, miR-4716, miR-4720, miR 4758, miR-4760, miR-4776-1, miR-4776-2, let-7a-2, let-7a*, let-7b, let-7c, let-7d, let-7e, let-7f, let-7g, let-7i, and the like.

In certain aspects, the lncRNAs of interest PCA3, PCGEM1, PCAT-1, MALAT1, GAS5, PCAT6, PCAT-18, lincRNA-p21, PRNCR1, TRPM2, CTBP1-AS, ANRIL, PVT1, SCHLAP1, HOTAIR, ZFAS1, HOTAIRM1, NEAT1, DANCR, HIF1A-AS, XIST, TOPORS-AS 1, LSINCT-5, MALAT1, LNP1, MALAT1, SPRY4-IT1, HNF1A-AS1, UCA1, HOTAIR, MEG3, CCAT1, MVIH, H19, CCAT2, AK126698, SOX2-OT, EVADR, PANDAR, BANCR, TUG1, CCAT1, CCAT1-L, CRNDE, E2F4, HULC, FER1L4, PTENP1, KCNQ1OT1, T-UCRs, OCC-1, CCAT1L, linc00152, HEIH, HOTTIP, DILC, LET, PCNA-AS1, TUC338, lncTCF7, CUDR, LALR1, UCA1, UCA1a, HOXD-AS1, TUG1, ncRAN, GHET1, linc-UBC1, SPRY4IT1, CRNDE, DLEU1, DLEU2, LUNAR1, BGL3, CCDC26, NALT, UCA1, lncRNAs linc-RoR, AF339813, AFAP1-AS, H19, HOST2, CDKN2B-AS, MEG3, PVT1, NBAT1, linc00963, CADM-AS1, RCCRT1, MALAT1, UCA1, linc00152, MRUL, GACAT2, GAS5, lncRNAs ADAMTS9-AS2, DISC2, CASC2, TSLC1-AS1, POU3F3.

In certain aspects, the proteins Pro2PSA, ROMA (HE4+CA-125), OVA1 (multiple proteins), HE4, Fibrin/fibrinogen degradation product (DR-70), AFP-L3%, Circulating Tumor Cells (EpCAM, CD45, cytokeratin 8, 18+, 19+), p63 protein, cKit, CA19-9, Estrogen receptor (ER), progesterone (PR), HER-2/neu, CA-125, CA15-3, CA27.29, Free PSA, Thyroglobulin, Nuclear Mitotic Apparatus protein (NuMA, NMP22), Alpha-fetoprotein (AFP), Total Carcinoembryonic antigen, Human hemoglobin (fecal occult blood), CD20, CD30, FIP1L1-PDGFRalpha, PDGFR, Philadelphia Chromosome (BCR/ABL), PML/RAR-alpha, TPMT, UGT1A1, EML4/ALK, KRAS, BRAF, leucine, isoleucine, valine. The designed biosensor in this invention can be adopted to detect any protein biomarkers including all biomarkers listed above, all long noncoding RNA listed above and all proteins listed above. Also, The biosensor can be additionally adopted to detect, circulation tumor DNA, enzymes, hormones or any biological fluids base biomarker detection.

In certain aspects, the disease state can be pancreatic ductal adenocarcinoma (PDAC), all other solid cancers and their subtypes, such as breast and ovarian cancer, uterine cancer, colorectal cancer, gastric cancer, cholangiocarcinoma, ampulla of Vater cancer, thyroid cancer, parathyroid cancer, head and neck cancer, esophageal cancer, liver cancer, kidney cancer, genito-urinary cancers, bladder and prostate cancer, mesothelioma, lung cancers, skin cancers such as basal cell carcinoma and squamous cell carcinoma and melanoma, other skin conditions such as skin rashes and psoriasis, glioblastomas and other central nervous system tumors, sarcomas, preneoplastic lesions and cystic lesions that may precede solid cancers, lymphoproliferative disorders such as leukemias, lymphomas, multiple myeloma, inherited cancers, and diseases other than cancer. Such diseases include, but are not limited to, diabetes mellitus, type I, type II, and pancreatogenic diabetes mellitus and the complications associated with these diabetes disorders, other endocrine and metabolic disorders, cardiovascular diseases include myocardial infarction, atherosclerosis, stroke, hypertension and its complications, vascular aneurysms, lipid disorders, inflammatory disorders of all organ systems including acute pancreatitis, hepatitis, cholangitis, colitis, glomerulonephritis, acute interstitial nephritis, and other acute inflammatory states, pulmonary disorders including chronic obstructive pulmonary diseases and pulmonary emboli, autoimmune disorders, gastrointestinal disorders including chronic pancreatitis, liver diseases including cirrhosis of the liver and steatohepatitis, chronic viral liver infections such as hepatitis B and C viruses, and kidney diseases, muscolo-skeletal disorders including but not limited to cancerassociated cachexia, muscular dystrophies and other degenerative muscle diseases, neuro-muscular disorders, rheumatoid arthritis, psoriatic arthritis, other inflammatory joint disease, crystal disease of the joint such as gout and pseudo-gout, degenerative arthritis, herniated disc disease, osteoporosis, ankylosing spondylitis, osteopetrosis, osteogenesis imperfect, spina bifida, scoliosis, spinal stenosis, traumatic spinal and brain injuries, neurological disorders such as neuro-generative disease and seizure disorders, Alzheimer's disease and other dementias, mental disorders including depression, bipolar disorders, schizophrenia, panic disorders, post-traumatic stress disorder (PTSD), concussion injuries that are either acute or chronic, chronic and acute infections whether bacterial, fungal, parasitic, helminthic, prion, protozoan such as malaria or babesiosis, infections with spirochetes, and generalized sepsis. In addition, the miR assays can be useful to assess intra-uterine disorders during pregnancy, and pregnancy associated conditions such as pre-eclampsia and eclampsia. The designed biosensor in this invention can be adopted to detect any diseases that above mentioned.

The biosensor according to the present invention can contribute to the development of a reliable POC system by quickly and accurately detecting at least one analyte used for diagnosing at least one of the various diseases described above or determining the degree thereof.

In addition, a luciferase protein tag may be attached to the surface of the $1^{st}$ GQD to ensure such is attached to a reaction strip (131) in a third region (130) to be described later to generate a detectable signal. The luciferase protein tag may be luciferin. The luciferin may produce a light signal as being oxidized to oxyluciferin by continuous action of ATP and luciferase. The luciferase protein tag attached to the $1^{st}$ GQD via direct thiol link or EDC/NHS coupling.

Additionally, a space can be attached to the surface of the $1^{st}$ GQD and the spacer may preferably be a PEG thiol-based compound.

The PEG thiol-based spacer provides an appropriate level of steric hindrance at the binding site of the biomarker attached to the surface of the $1^{st}$ GQD, thereby preventing the biomarker from forming non-specific binding with other substances than the analyte.

Accordingly, the size and length of the PEG thiol-based spacer may vary depending on the type and size of the target analyte of the biomarker attached to the surface of the $1^{st}$ GQD. As such, the $1^{st}$ GQD can induce selective binding of an analyte specific to a biomarker attached to the surface of the $1^{st}$ GQD by designing the size and length of the PEG thiol-based spacer appropriately based on the type and size of a target analyte.

Figure 16:
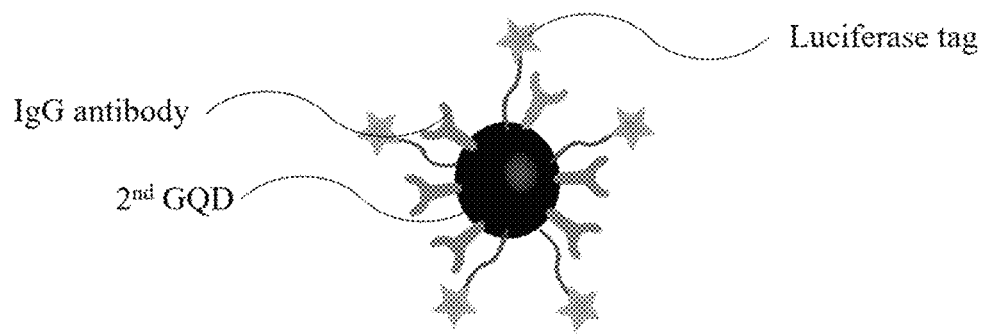
FIG. 16 is a schematic view of a GQD contained in a second region to bind with control line of the test region of the test kit shown in FIG. 1. This GQDs will not bind with any analyte in this region.

FIG. 16 is a schematic view of a $2^{nd}$ GQD included in the second region (120) of the biosensor shown in FIG. 1. Referring FIG. 16, IgG antibody such as anti-mouse IgG antibody is attached to the surface of a $2^{nd}$ GQD. The IgG antibody serves as a medium that allows selective attachment to the control strip (133) in the third region (130) to be described later.

In addition, as with the $1^{st}$ GQD, a luciferase protein tag may be attached to a surface of the $2^{nd}$ GQD to generate a detectable signal in the third region (130) to be described later. The luciferase protein tag is attached to the $2^{nd}$ GQD via direct thiol link and EDC/NHS coupling. The bodily fluid sample moved to the second region (120) can react with at least one $1^{st}$ GQD specific to at least one analyte of the fluid sample in the second region (120) while it is moved due to the lateral flow capillary action. Likewise, the $2^{nd}$ GQD also can move in the same direction as the flow of the bodily fluid sample.

The bodily fluid sample is moved to the third region (130) by the lateral flow capillary action.

The third region (130) is a reaction pad region that allows the GQD coupled with the analyte of the bodily fluid sample moved by the lateral flow capillary action from the second region (120) to react with a reaction strip (131) to produce a detectable signal.

The third region (130) has at least one reaction strip (131) that detects the presence of the $1^{st}$ GQD coupled with the analyte and a control strip (133) that detects the presence of the $2^{nd}$ GQD not coupled with the analyte.

Figure 19:
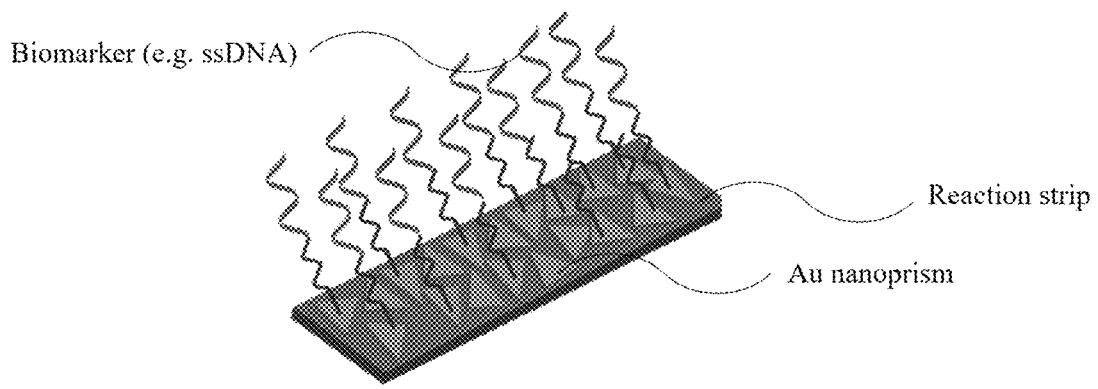
FIG. 19 and FIG. 20 are schematic views of some examples of reaction strips provided in a third region of the cartridge shown in FIG. 1.
Figure 20:
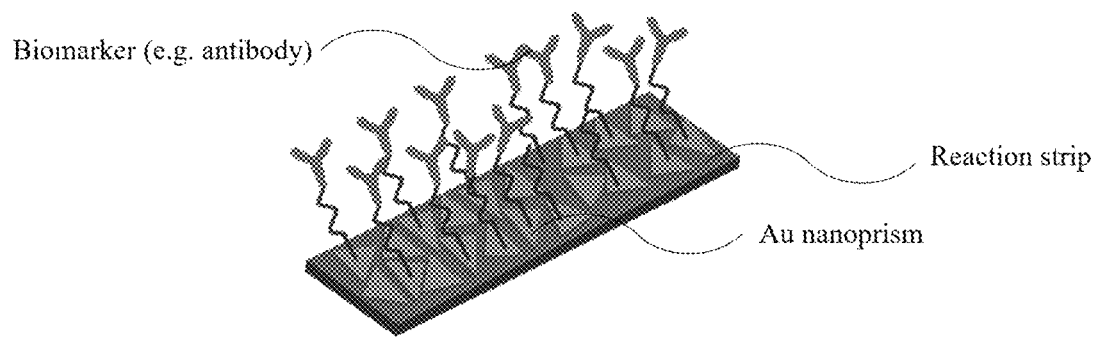
Figure 21:
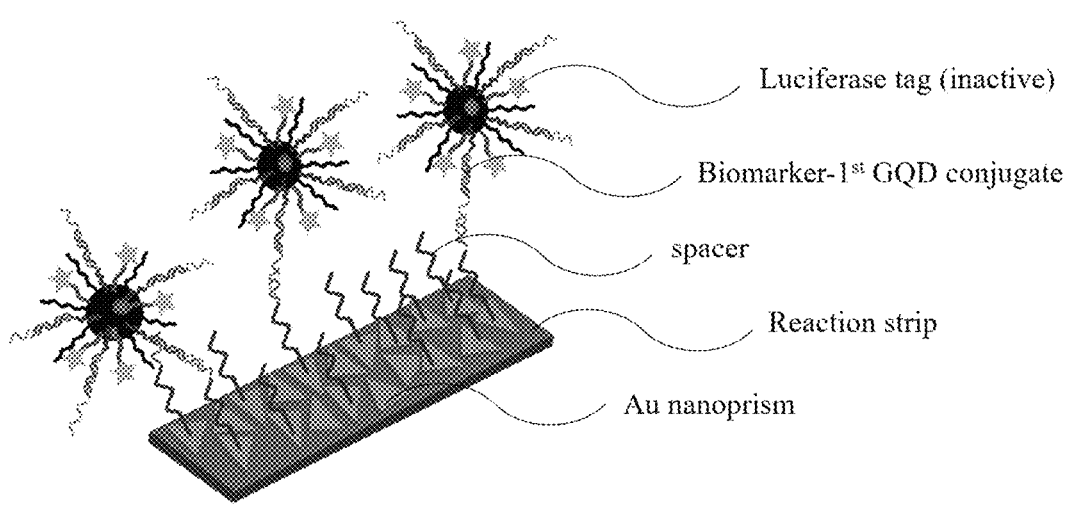
FIG. 21 are FIG. 22 are schematic views of some examples of reaction strips provided in a third region of the cartridge shown in FIG. 1.
Figure 22:
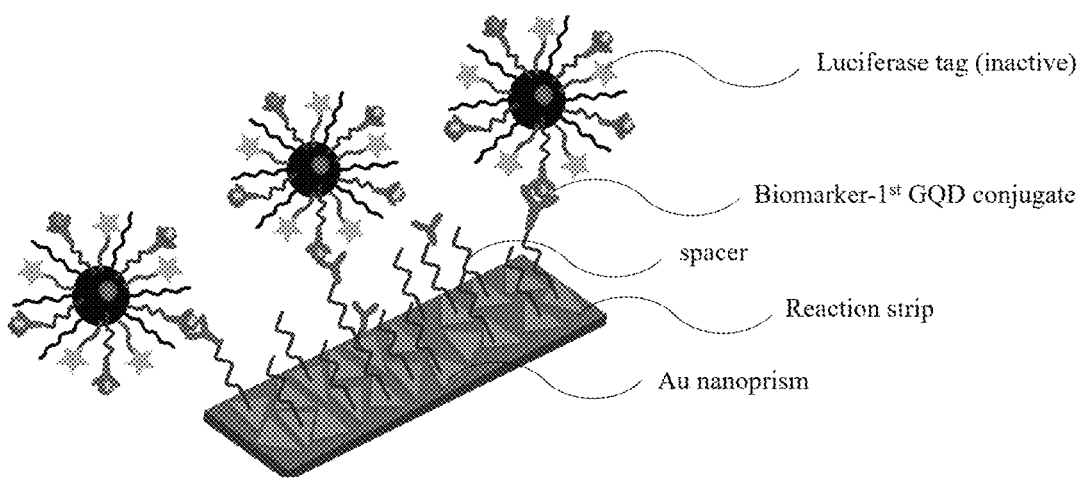

FIG. 19 and FIG. 20 are schematic views of some examples of the reaction strips in the third region of the biosensor shown in FIG. 1, and FIG. 21 and FIG. 22 are schematic views of examples of inactive state of the luciferase tags of the $1^{st}$ GQDs coupled with analytes on the reaction strip shown in FIG. 19 and FIG. 20.

Figure 8:
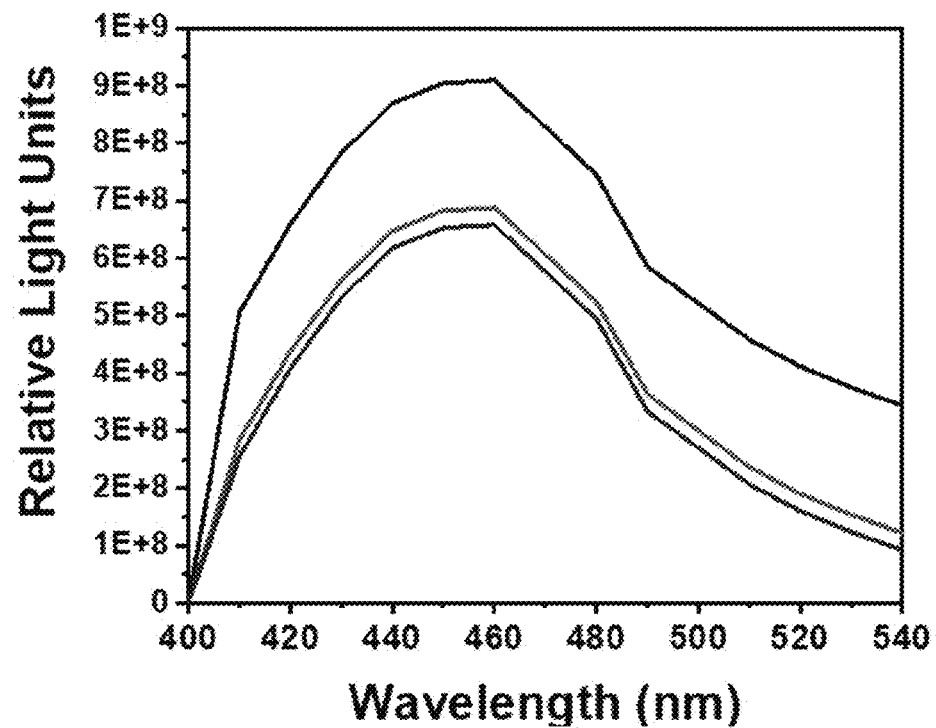
FIG. 8 is recorded light intensity for bioluminescence for $PEG_8$ acetic acid functionalized nanoparticles after binding with 100% Luciferase (black line), Luciferase and NMP22 antibody (1:1)-black line and Luciferase, NMP22 and Biotin (1:1:1)-blue line.

Referring FIG. 7 and FIG. 8 a reaction strip (131), as with the $1^{st}$ GQD, comprises a biomarker such as ssDNA and/or antibody specific to the analyte depending on the type of the target analyte.

Accordingly, the $1^{st}$ GQD coupled with the analyte that is moved by the lateral flow capillary action, can be attached to the reaction strip (131) corresponding to the type of the analyte through complementary binding.

In the case of a biomarker in the reaction strip (131), the target analyte is the same as that of the biomarker attached to the surface of the $1^{st}$ GQD, and thus detailed explanation will not be given herein.

Figure 23:
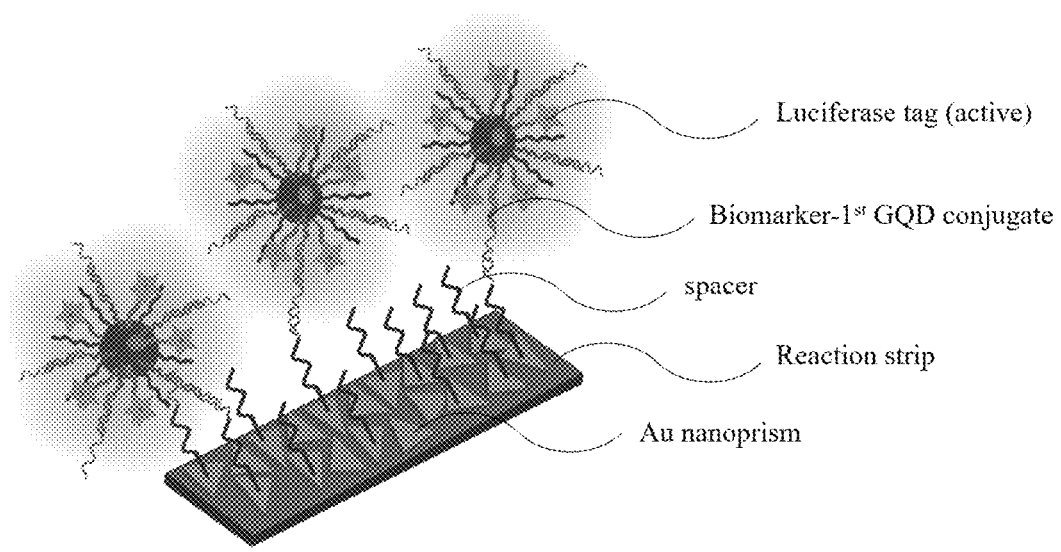
FIG. 23 and FIG. 24 are schematic views of active state of a luciferase tag of $1^{st}$ GQD shown in FIG. 17 and FIG. 18. After bound to the test strip.
Figure 24:
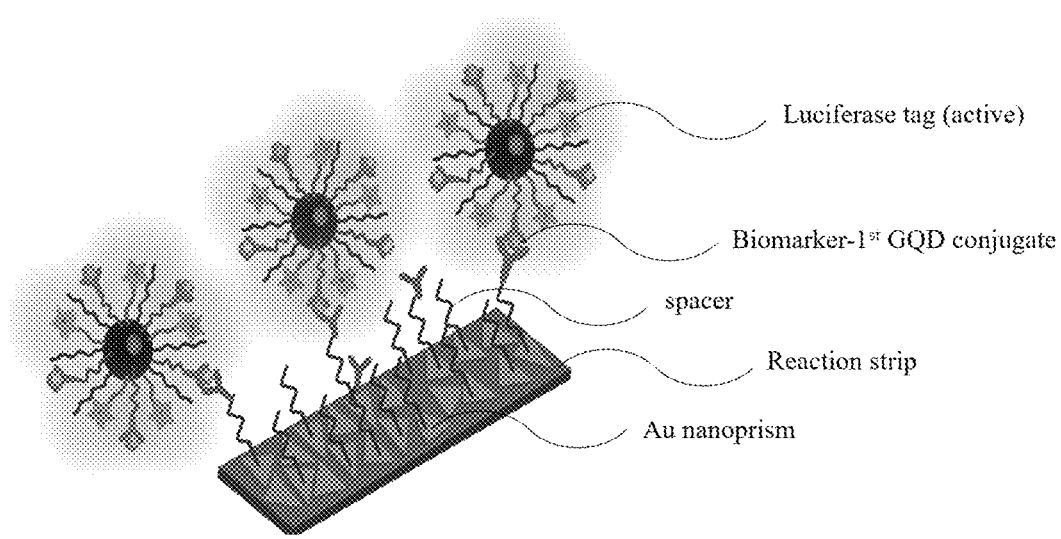

In addition, the biomarker is attached to Au nanoprism on the reaction strip (131). The Au nanoprism may display unique localized surface plasmon resonance properties and be self-assembled in the trigonal form. When the biomarker attached to the au nanoprism and the $1^{st}$ GQD are bound via common target analyte, plasmon coupling is further enhanced bioluminescence effect induced by luciferases. The Au nanoprism has edge length range of 10 nm to 150 nm, and electromagnetic radiation having a wavelength between 350 nm to 1200 nm. In addition, the Au nanoprism is triangular nanoprism, Au nano spherical particle, Au nanorod, and/or Au star can be used and here with explained the sensitivity when using Au SPs FIG. 22 and FIG. 23 are schematic views of active state of the luciferase tags of the $1^{st}$ GQD shown in FIG. 17 and FIG. 18, respectively.

Figure 17:
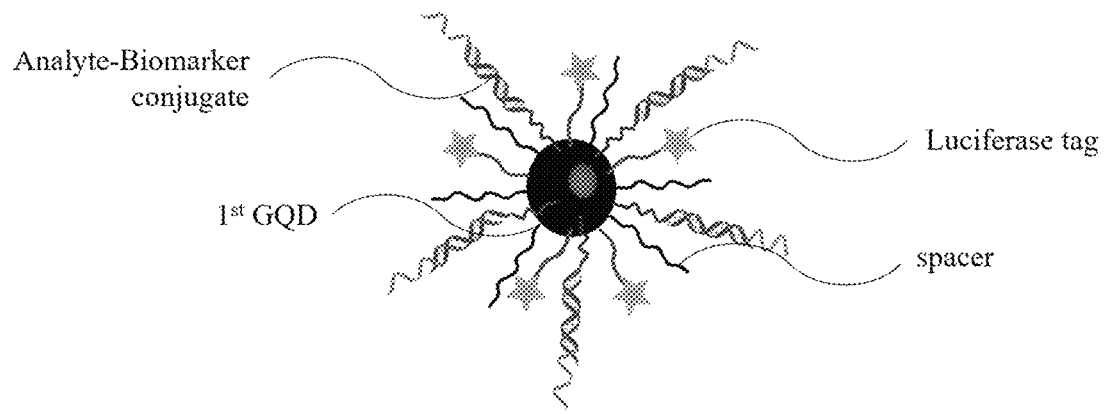
FIG. 17 and FIG. 18 are schematic views of the test strip region after binding with the target analyte containing GQDs explained in FIG. 14 and FIG. 15 and here inactive state of a luciferase tag.
Figure 18:
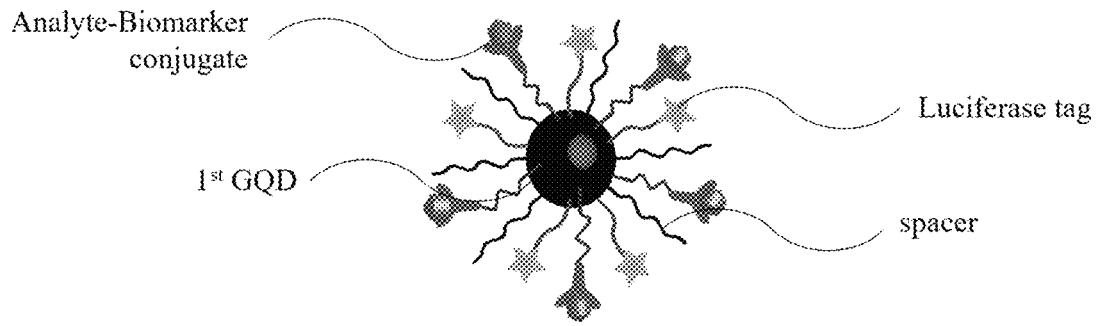

For the luciferase tags of the $1^{st}$ GQD shown in FIG. 17 and FIG. 18 to become an active state, the luciferase tags in the inactive state needs to be activated by the luciferases.

For that, an enzyme storage (132) where luciferase is stored is placed adjacent to the reaction strip (131), and the enzyme storage (132) may release the luciferase into the reaction strip (131). This may also can achieved by directly adding enzyme buffer after urine sample reaching to the absorbent pad In addition, the enzyme storage (132) is present with a solution containing not only luciferase but also $Mg^{2+}$ and ATP, and they are discharged into the reaction strip (131) along with the luciferase to activate luciferin, which is a luciferase protein tag of the $1^{st}$ GQD attached to the reaction strip (131). As such, the activated luciferin may emit a detectable signal and such light signal can be detected by the POC system to be described later.

Luc+LH2+ATP→Luc·LH2-AMP+PPi
Luc☐LH2-AMP+O2→Luc☐AMP☐Oxyluciferin*+CO2
Luc☐AMP☐Oxyluciferin*→Luc+Oxyluciferin+AMP+hv Additionally, a spacer is attached onto the au nanoprism in the reaction strip (131), and the spacer may be preferably a PEG thiol-based compound.

The PEG thiol-based spacer provides an appropriate level of steric hindrance at the binding site of the biomarker attached onto the au nanoprism, thereby preventing the biomarker from forming non-specific binding with other substances than the analyte.

Accordingly, the size of the PEG thiol used for this study was 1000 g/mol and length of the PEG thiol-based spacer may vary depending on the type and size of the target analyte targeted by the biomarker attached onto the au nanoprism. As such, the au nanoprism can induce selective binding of the $1^{st}$ GQD coupled with an analyte specific to the biomarker attached onto the surface of the au nanoprism by designing the size and length of the PEG thiol-based spacer appropriately based on the type and size of a target analyte. As shown in FIG. 1, the reaction strip (131) may be provided in plurality depending on the type of the target analyte.

For example, the third region (130) may sequentially have a first reaction strip (131a) with a biomarker 5'-SH-C3-ssDNA-10b targeting microRNA 10b, a second reaction strip (131b) with a biomarker ssDNA-C3-UCA targeting lncRNA UCA, and a third reaction strip (131c) with a biomarker NMP anti-body targeting NMP proteins.

As a plurality of $1^{st}$ GQDs coupled with specific analyte are moved to the third region (130) due to lateral flow capillary action, they will be captured sequentially on the reaction strip (131) with a biomarker specific to the analyte.

As such, if a plurality of reaction strips (131) are provided, a plurality of analytes may be detected using one biosensor (100), and furthermore, it is possible to diagnose a disease more accurately based on the a plurality of analytes or different diseases corresponding to different analytes.

The $1^{st}$ GQD and $2^{nd}$ GQD to which the analytes are unbound can pass through the third region (130) without being captured by the reaction strip (131 However, the $2^{nd}$ GQD may be captured by a control strip (133) positioned downstream of the reaction strip (131).

Figure 25:
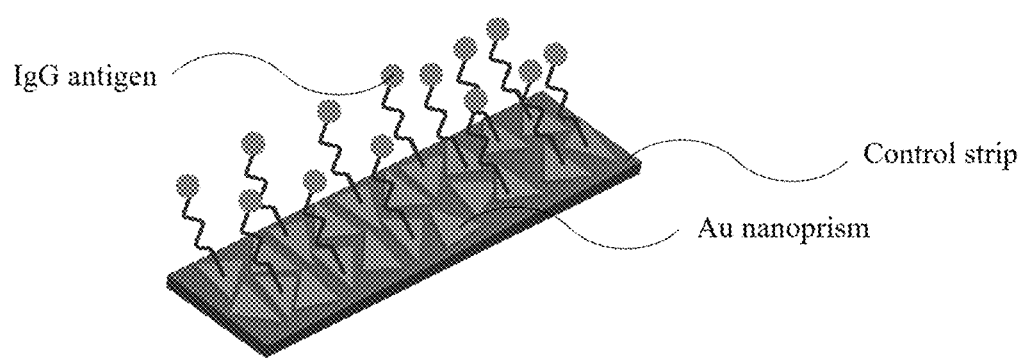
FIG. 25 is a schematic view of a control strip in a third region of the cartridge shown in FIG. 1
Figure 26:
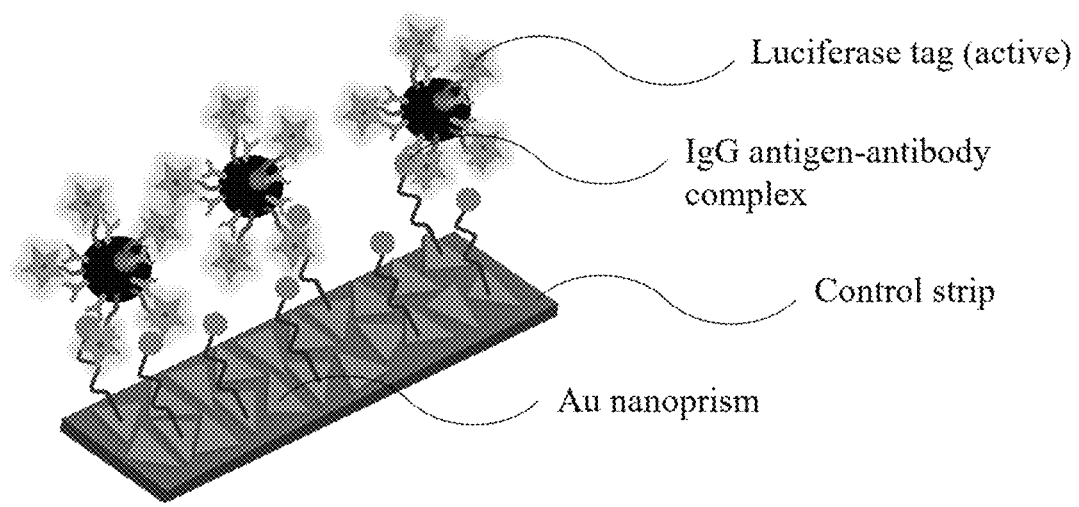
FIG. 26 is a schematic view of a $2^{nd}$ GQD in FIG. 16 is coupled to the control strip shown in FIG. 25.
Figure 27:
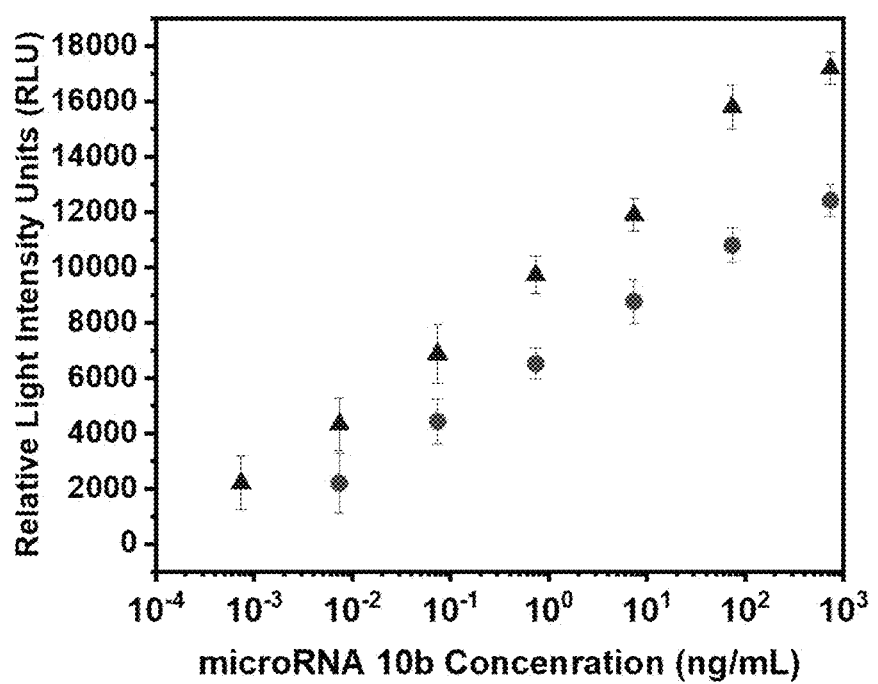
FIG. 27 shows the calibration plot for microRNA 10b. Blue Triangles shows the calibration plot using triangular nanoprisms on to test strip and red circles represents the calibration plot using gold spherical particles on to the test strips. Obtained RLU values with standard deviation summarized in Table 10 LOD sensitivities are summarized in the Table 9. All calibration plots were prepared in human urine
Figure 28:
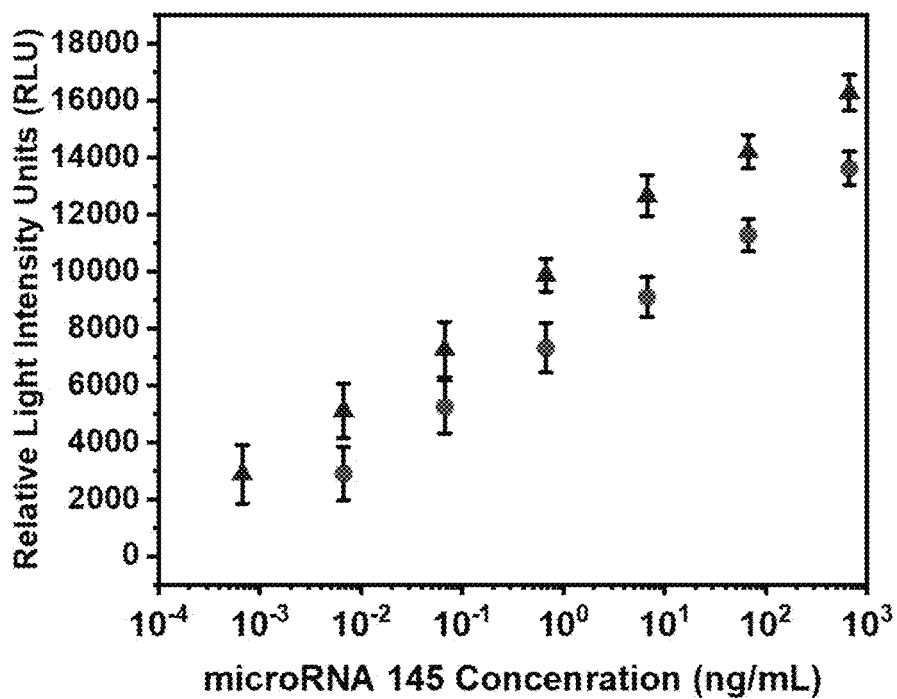
FIG. 28 shows the calibration plot for microRNA 145. Blue Triangles shows the calibration plot using triangular nanoprisms on to test strip and red circles represents the calibration plot using gold spherical particles on to the test strips. Obtained RLU values with standard deviation summarized in Table 10 LOD sensitivities are summarized in the Table 9. All calibration plots were prepared in human urine
Figure 29:
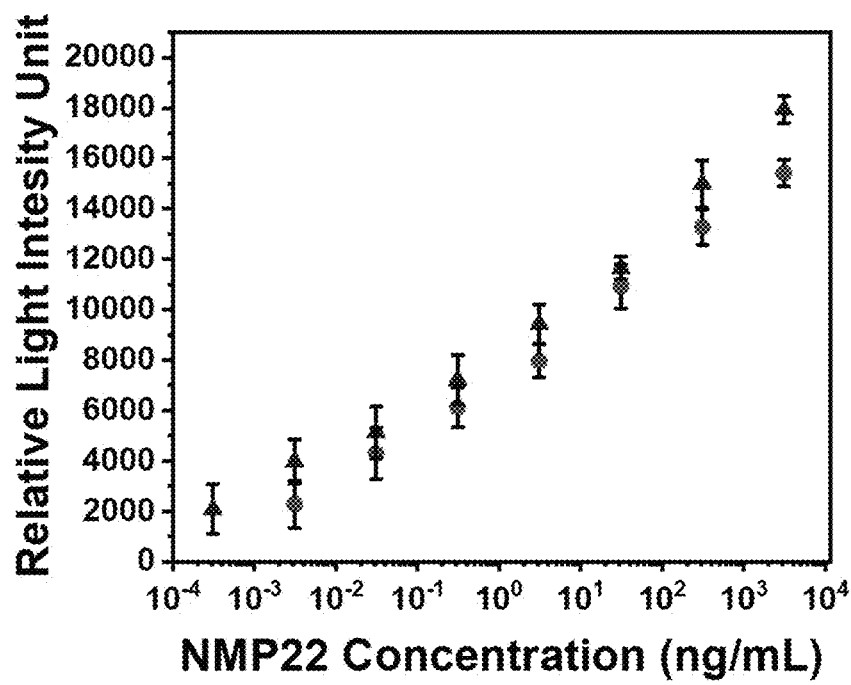
FIG. 29 shows the calibration plot for NMP22. Blue Triangles shows the calibration plot using triangular nanoprisms on to test strip and red circles represents the calibration plot using gold spherical particles on to the test strips. Obtained RLU values with standard deviation summarized in Table 10 LOD sensitivities are summarized in the Table 9. All calibration plots were prepared in human urine
Figure 30:
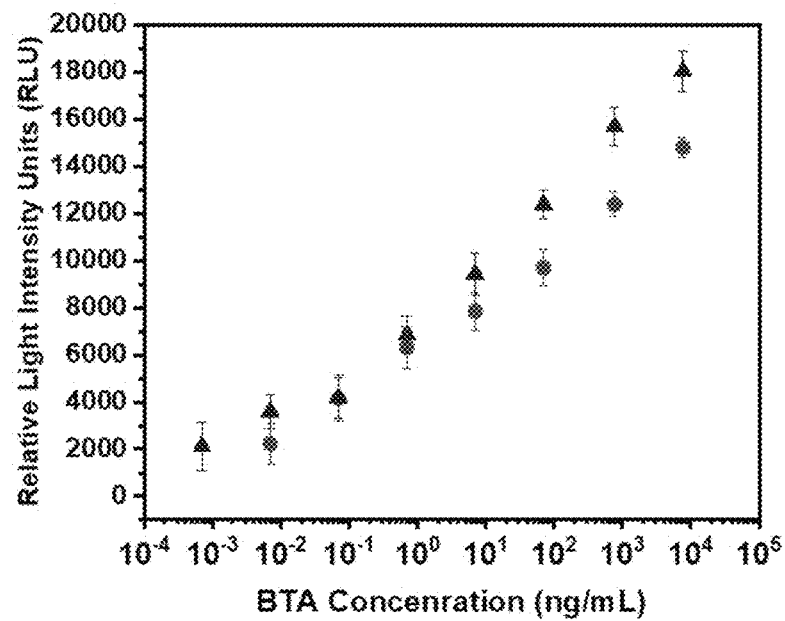
FIG. 30 shows the calibration plot for BTA. Blue Triangles shows the calibration plot using triangular nanoprisms on to test strip and red circles represents the calibration plot using gold spherical particles on to the test strips. Obtained RLU values with standard deviation summarized in Table 10 LOD sensitivities are summarized in the Table 9. All calibration plots were prepared in human urine
Figure 31:
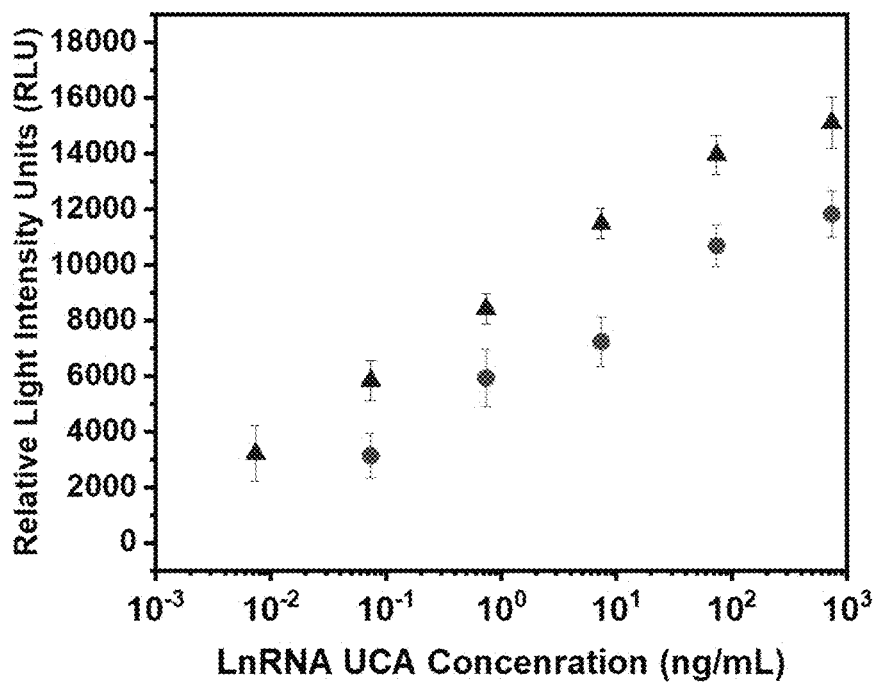
FIG. 31 shows the calibration plot for lnRNA UCA. Blue Triangles shows the calibration plot using triangular nanoprisms on to test strip and red circles represents the calibration plot using gold spherical particles on to the test strips. Obtained RLU values with standard deviation summarized in Table 10 LOD sensitivities are summarized in the Table 9. All calibration plots were prepared in human urine

FIG. 25 is a schematic view of a control strip in the third region of the biosensor shown in FIG. 1, and FIG. 26 is a schematic view of $2^{nd}$ GQDs being bound to the control strip shown in FIG. 25.

Referring to FIG. 25, a control strip (133) contains IgG antigens specific to IgG antibodies attached to the $2^{nd}$ GQDs. Accordingly, the $2^{nd}$ GQDs moved by the lateral flow capillary action may be attached to the control strip (133) via antigen antibody immune response.

Here, the IgG antigen is attached onto the au nanoprism in the control strip (133). The au nanoprism may have unique localized surface plasmon resonance properties and be self-assembled in the trigonal form. If the IgG antigen attached onto the au nanoprism and IgG antigen attached to $2^{nd}$ GQD are bound together via antigen-antibody immune response, such plasmon coupling may further enhance bioluminescence effect induced by luciferases. As with the $1^{st}$ GQD, for the $2^{nd}$ GQD to produce the aforementioned bioluminescence effect, the luciferase tags attached to the $2^{nd}$ GQD should be activated into active state by luciferases. The activation mechanism of the luciferase tags attached to the $2^{nd}$ GQD is the same as that of the $1^{st}$ GQD, and thus will not be described herein.

As such, the bioluminescence induction response based on the antigen antibody immune response occurring in the control strip (133) serves as a means to identify whether the bodily fluid sample has moved due to the lateral flow capillary action from the second region (120) to the third region (130).

Separated the bodily flow sample, which is a unreacted substance in the third region (130) of the bodily flow sample moving within the biosensor(100) due to the lateral flow capillary action (remaining substances excluding GQDs captured by the reaction strip (131) and the control strip (133)) can pass through the third region (130) and move to the fourth region (140).

The fourth region (140) is an absorption pad region that absorbs and removes the separated the bodily fluid sample moved from the third region (130) by the lateral flow capillary action.

A buffered solution may additionally be added to the biosensor to enhance the absorption of the separated the bodily fluid sample by the fourth region (140).

In addition, according to another aspect of the present invention, a POC system is provided, comprising i) a biosensor as described above; ii) at least one biosensor chamber into which the biosensor is inserted; and iii) a detection assembly that individually detects light signals emitted from at least one the reaction strip in the biosensor inserted into the biosensor chamber.

The POC system may be an independent terminal or a dependent terminal accessible to information processing means such as a computer, a mobile phone, a tablet, and so forth. The bodily fluid sample containing the analyte is introduced into the biosensor to generate a detectable signal via at least one biological and/or chemical reaction, and the presence of a disease and/or the degree of the disease can be diagnosed by qualitatively and/or quantitatively detecting the light signal emitted from at least one reaction strip in the biosensor after inserting the biosensor into the biosensor chamber in the POC system.

In addition, a separate code that can assign unique ID, identification symbol or address (hereinafter, identification information) is embedded in the biosensor, and thus if the biosensor is inserted into the biosensor chamber of the POC system, unique identification information corresponding to the biosensor and the identification information can be matched to diagnosis information such as the presence of a disease and/or the degree of the disease of the patient read by the biosensor.

The POC system may contribute to the development of a reliable POC system by quickly and accurately detecting at least one analyte used for diagnosing at least one disease or determining the degree thereof through one biosensor.

In addition, in another embodiment, the biosensor used in the POC system has a plurality of reaction strips to diagnose different diseases or determine the degrees thereof, and therefore, diagnosing multiple diseases and/or determining the degrees thereof can also be performed simultaneously by detecting a signal coming from the biosensor after one biosensor is inserted to the biosensor chamber.

As such, upon completion of analysis on the biosensor, the results of the analysis may be transmitted to a terminal such as a computer, mobile phone or tablet by wire and/or wirelessly, or to the POC system's server of a managing party. In this case, the managing party may be a state, a public institution, or a medical institution. Unlike the POC system illustrated in FIG. 1, in the case of POC system could be a plurality of biosensors ($1^{st}$ biosensor and $2^{nd}$ biosensor) may be inserted into the biosensor chamber of the POC system.

For example, the biosensor used in the POC system has a plurality of reaction strips for individually determining multiple analytes for the purpose of diagnosing a disease or determining the degree of the disease, and therefore the accuracy and reliability of the diagnosis and/or determination via single biosensor may be further enhanced.

In addition, in the case of POC system, simultaneous analysis of a plurality of biosensors is possible and thus it has the advantage of performing diagnosis and/or determination of a disease by selectively inserting a biosensor as needed by medical practitioner or user.

Above, while the examples of the present invention have been described, it will be understood by those of ordinary skill in the art that the present invention may be changed and modified in various ways by addition, alternation, or deletion of components without departing from the spirit of the present invention defined in the appended claims.

The invention claimed is:

1. A biosensor for detecting an analyte in a bodily fluid sample, comprising:
   I. a first region that houses the bodily fluid sample,
   II. a second region positioned downstream of the first region, wherein the bodily fluid sample housed in the first region is moved by lateral flow capillary action, wherein the second region comprises a graphene quantum dots (GQDs) mixture and the mixture comprises a 1st graphene quantum dot (GQD), wherein the 1st graphene quantum dot is specific to the analyte and a 2nd GQD, wherein the 2nd GQD is specific to a control strip,
   III. a third region positioned downstream of the second region, wherein the GQDs mixture is moved by lateral fluid capillary action to the third region, wherein the third region comprises at least one reaction strip that detects the presence of the 1st GQD to which the analyte is bound and a control strip that detects the presence of the 2nd GQD, wherein the control strip is downstream from the reaction strip.

2. The biosensor according to claim 1, wherein:
the bodily fluid sample comprises at least one sample selected from the group consisting of whole blood, human plasma, bovine plasma, phosphate buffered saline, water, serum, saliva, urine, tears, pancreatic juice, bile juice, saliva, peritoneal fluid, gastric juice, digestive juice, bone marrow, cerebrospinal fluid, stools, semen, vaginal fluid, mucosa and fluid extracted from tissue.

3. The biosensor according to claim 1, wherein:
the diameter of the 1st and 2nd GQD is between 5 nm and 100 nm, and the 1st and 2nd GQD appear in the UV-vis spectrum in the range of 350 nm to 750 nm.

4. The biosensor according to claim 1, wherein:
   I. the 1st GQD comprises a luciferase protein tag and an ssDNA and/or antibody, specific to the analyte, attached to the 1st GQD surface; and
   II. the 2nd GQD comprises a luciferase protein tag and an IgG antibody attached to the 2nd GQD surface.

5. The biosensor according to claim 4, wherein:
the 1st GQD comprises the ssDNA.

6. The biosensor according to claim 5, wherein:
the ssDNA is attached to the 1st GQD via thiol or amine functionalized ssDNA.

7. The biosensor according to claim 4, wherein:
the 1st GQD comprises the antibody.

8. The biosensor according to claim 4, wherein:
the luciferase protein tag is attached to the 1st GQD and/or 2nd GQD via direct thiol link or EDC/NHS coupling.

9. The biosensor according to claim 4, wherein the ssDNA and/or antibody is attached to the 1st GQD surface through a PEG thiol-based spacer.

10. The biosensor according to claim 1, further comprises:
an enzyme storage that releases a luciferase to the reaction strip in the third region.

11. The biosensor according to claim 10, wherein:
the luciferase is either firefly luciferase, NLuc or *Gaussia* luciferase.

12. The biosensor according to claim 4, wherein:
the reaction strip comprises,
  I. an Au nano prism; and
  II. a ssDNA and/or antibody attached to the Au nano prism, and specific to the analyte.

13. The biosensor according to claim 12, wherein:
the Au nano prism has edge length range of 10 nm to 150 nm, and electromagnetic radiation having a wavelength between 350 nm to 1200 nm.

14. The biosensor according to claim 12, wherein the ssDNA and/or antibody is attached to the Au nano prism in the reaction strip through a PEG thiol-based spacer.

15. The biosensor according to claim 4, wherein
the reaction strip comprises a nanostructure selected from an Au triangular nano prism, an Au nano spherical particle, an Au nanorod, and/or Au nanostar; wherein the ssDNA and/or antibody is attached to the nanostructure.

16. The biosensor according to claim 4, further comprising:
a fourth region positioned downstream of the third region, in which separated the bodily fluid sample is absorbed.

17. The biosensor according to claim 4, wherein
the ratio of luciferase to ssDNA is 1:1, 1:5, 1:10, 1:50, or 1:100; or the ratio of luciferase to antibody is 1:1, 1:5, 1:10, 1:50, or 1:100.

18. A biosensor for detecting an analyte in a bodily fluid sample, comprising a first region, a second region, and a third region, connected by means providing for lateral flow capillary action, wherein
  a) the first region comprises a housing for the bodily fluid sample,
  b) the second region comprises a first quantum dot, wherein the first quantum dot specifically binds to the analyte and a second quantum dot, wherein the second quantum dot specifically binds a control strip; and
  c) the third region comprises (i) a reaction strip that binds to the analyte; and (ii) the control strip; wherein the first quantum dot and second quantum dot is either a semiconductor quantum dot or a graphene quantum dot, wherein the control strip is downstream from the reaction strip.

19. The biosensor of claim 18, wherein the first quantum dot is a first graphene quantum dot and the second quantum dot is a second graphene quantum dot.

20. The biosensor of claim 19, wherein the first graphene quantum dot comprises a first antibody or a first single-stranded nucleic acid specific for the analyte; and the reaction strip further comprise a second antibody or a second single-stranded nucleic acid specific for the analyte.

21. The biosensor of claim 20, wherein the second graphene quantum dot further comprises an IgG antibody, and the control strip further comprises an antigen to which the IgG antibody binds.

22. The biosensor of claim 21, wherein the first graphene quantum dot comprises a first luciferase tag and the second graphene quantum dot comprises a second luciferase tag, wherein the diameter of the first quantum dot and second quantum dot is each between 5 nm and 100 nm, and the first quantum dot and second quantum dot emit in the range of 350 nm to 750 nm.

23. The biosensor of claim 22, wherein the first and second luciferase tag is luciferin.

24. The biosensor of claim 23, further comprising an enzyme storage that releases luciferase to the reaction strip in the third region.

25. The biosensor of claim 24, wherein the luciferase is either firefly luciferase, NLuc or *Gaussia* luciferase.

26. The biosensor of claim 21, wherein the reaction strip comprises a gold nanostructure.

27. The sensor of claim 26, wherein the gold nanostructure is an Au triangular nano prism, an Au nano spherical particle, an Au nanorod, or an Au nanostar.

28. The biosensor of claim 26, wherein the gold nanostructure is attached to the second antibody, or the second single-stranded nucleic acid, through a PEG thiol-based spacer attached onto the reaction gold nanostructure surface.

29. The biosensor of claim 21, wherein the first graphene quantum dot is attached to the first antibody, or the first single-stranded nucleic acid, through a PEG thiol-based spacer.

30. The biosensor of claim 21, wherein the second graphene quantum dot IgG antibody is an anti-mouse IgG and the control strip antigen is a mouse antigen.

31. The biosensor of claim 18, wherein the means providing for lateral flow capillary action comprises a glass fiber, a cellulose filter or a nitrocellulose membrane.

32. The biosensor of claim 21, wherein the means providing for lateral flow capillary action comprises a glass fiber or cellulose filter.

33. The biosensor of claim 32, wherein the biosensor further comprises a fourth region where the bodily sample material is absorbed.

34. The biosensor of claim 33, comprising a plurality of reaction strips for detecting a plurality of analytes.

35. The biosensor of claim 18, wherein
  a) the first quantum dot is a first semi-conductor quantum dot comprising a luciferase tag; and
  b) the second quantum dot is a second semi-conductor quantum dot comprises a luciferase tag.

36. The biosensor of claim 35, wherein the means providing for lateral flow capillary action comprises a nitrocellulose membrane, glass fiber or cellulose filter; and the biosensor further comprises a fourth region where the bodily sample material is absorbed.

* * * * *

SEQUENCE LISTING

<160> NUMBER OF SEQ ID NOS: 9

<210> SEQ ID NO 1
<211> LENGTH: 35
<212> TYPE: DNA
<213> ORGANISM: Artificial Sequence
<220> FEATURE:
<223> OTHER INFORMATION: Modified 10b ssDNA

<400> SEQUENCE: 1
cacaaattcg gttctacagg gtaggggggg ggggg        35

<210> SEQ ID NO 2
<211> LENGTH: 23
<212> TYPE: RNA
<213> ORGANISM: Artificial Sequence
<220> FEATURE:
<223> OTHER INFORMATION: MicroRNA 10b

<400> SEQUENCE: 2
uacccuguag aaccgaauuu gug        23

<210> SEQ ID NO 3
<211> LENGTH: 34
<212> TYPE: DNA
<213> ORGANISM: Artificial Sequence
<220> FEATURE:
<223> OTHER INFORMATION: Modified 145 ssDNA

<400> SEQUENCE: 3
agggattcct gggaaaactg gacccccccc cccc        34

<210> SEQ ID NO 4
<211> LENGTH: 23
<212> TYPE: RNA
<213> ORGANISM: Artificial Sequence
<220> FEATURE:
<223> OTHER INFORMATION: MicroRNA 145

<400> SEQUENCE: 4
guccaguuuu cccaggaauc ccu        23

<210> SEQ ID NO 5
<211> LENGTH: 70
<212> TYPE: DNA
<213> ORGANISM: Artificial Sequence
<220> FEATURE:
<223> OTHER INFORMATION: Modified ssDNA for UCA 1

<400> SEQUENCE: 5
ccggggtaat gtatcatcgg cttagctcga gctaagccga tgatacatta ccttttttgtt        60 tttttttttt        70

<210> SEQ ID NO 6
<211> LENGTH: 58
<212> TYPE: RNA
<213> ORGANISM: Artificial Sequence
<220> FEATURE:
<223> OTHER INFORMATION: UCA1 Long noncoding RNA 5'3'

<400> SEQUENCE: 6

```
ggccccauua cauaguagcc gaaucgagcu cgauucggcu acuauguaau ggaaaaac        58

<210> SEQ ID NO 7
<211> LENGTH: 12
<212> TYPE: DNA
<213> ORGANISM: Artificial Sequence
<220> FEATURE:
<223> OTHER INFORMATION: Test line sequence for ssDNA-10b

<400> SEQUENCE: 7
cccccccccc cc                                                         12

<210> SEQ ID NO 8
<211> LENGTH: 12
<212> TYPE: DNA
<213> ORGANISM: Artificial Sequence
<220> FEATURE:
<223> OTHER INFORMATION: Test line sequence for ssDNA-145

<400> SEQUENCE: 8
gggggggggg gg                                                         12

<210> SEQ ID NO 9
<211> LENGTH: 12
<212> TYPE: DNA
<213> ORGANISM: Artificial Sequence
<220> FEATURE:
<223> OTHER INFORMATION: Test line sequence for UCA1

<400> SEQUENCE: 9
aaaaaaaaaa aa                                                         12
```